US012626512B2

(12) United States Patent
Walz et al.

(10) Patent No.: US 12,626,512 B2
(45) Date of Patent: May 12, 2026

(54) CLINICAL MONITORING DEVICE

(71) Applicant: HYPROS GMBH, Stralsund (DE)

(72) Inventors: Marcel Walz, Stralsund (DE); Tobias Gebhardt, Rostock (DE)

(73) Assignee: HYPROS GMBH, Stralsund (DE)

( * ) Notice: Subject to any disclaimer, the term of this patent is extended or adjusted under 35 U.S.C. 154(b) by 394 days.

(21) Appl. No.: 18/250,453

(22) PCT Filed: Aug. 6, 2021

(86) PCT No.: PCT/EP2021/072099
§ 371 (c)(1),
(2) Date: Apr. 25, 2023

(87) PCT Pub. No.: WO2022/089803
PCT Pub. Date: May 5, 2022

(65) Prior Publication Data
US 2024/0013544 A1     Jan. 11, 2024

(30) Foreign Application Priority Data

Oct. 26, 2020    (WO) ................. PCT/EP2020/080040

(51) Int. Cl.
*G06V 20/52*     (2022.01)
*G16H 40/20*     (2018.01)
*G16H 50/30*     (2018.01)

(52) U.S. Cl.
CPC ............. *G06V 20/52* (2022.01); *G16H 40/20* (2018.01); *G16H 50/30* (2018.01)

(58) Field of Classification Search
CPC ........ G06V 20/52; G16H 40/20; G16H 50/30; G16H 30/00; G03B 17/02; G03B 17/561; G08B 21/0407; G08B 21/245
See application file for complete search history.

(56) References Cited

U.S. PATENT DOCUMENTS 8,094,029 B2     1/2012 Ortiz et al.
8,368,544 B2     2/2013 Wildman et al.
(Continued)

FOREIGN PATENT DOCUMENTS

AU     2010322439 B2     5/2014
AU     2012335735 B2     10/2015
(Continued)

OTHER PUBLICATIONS

Applicant: GWA Hygiene GMBH; "Clinical Monitoring Device"; International Application No. PCT/EP2021/062099 Filed: Aug. 6, 2021; PCT International Search Report and Written Opinion; Examiner: Ralph Ruckerl; dated Feb. 16, 2022; 24 pgs.

*Primary Examiner* — Christopher Wait
(74) *Attorney, Agent, or Firm* — Tarolli, Sundheim, Covell & Tummino LLP

(57)     ABSTRACT

A clinical monitoring device, in particular a patient zone monitoring device is described. The monitoring device comprises a first sensing unit comprising at least one first sensor configured to acquire spatial data representing spatially resolved depth information with respect to a first field of view of the first sensing unit, a second sensing unit comprising at least one second sensor configured to acquire thermal data representing spatially resolved temperature information with respect to a second field of view of the second sensing unit, and a processing unit comprising at least one processor, the processing unit being configured to receive the spatial data from the first sensing unit and the thermal data from the second sensing unit and process at least the spatial data and the thermal data to generate scene data representing information with respect to a scene in a volume comprised in at least one of the first field of view and the second field of view.

19 Claims, 10 Drawing Sheets

(56) References Cited

U.S. PATENT DOCUMENTS

| | | | |
|---|---|---|---|
| 8,400,309 | B2 | 3/2013 | Glenn et al. |
| 8,810,388 | B2 | 8/2014 | Jacobs et al. |
| 9,195,799 | B2 | 11/2015 | Sze et al. |
| 9,270,319 | B2 | 2/2016 | Bietz et al. |
| 9,325,920 | B2 | 4/2016 | Van Nieuwenhove et al. |
| 9,390,302 | B2 | 7/2016 | Bassan-Eskenazi et al. |
| 9,753,131 | B2 | 9/2017 | Adib et al. |
| 9,817,298 | B1 | 11/2017 | Dhall et al. |
| 10,031,078 | B2 | 7/2018 | Ritter et al. |
| 10,034,979 | B2 | 7/2018 | Bechtel et al. |
| 10,342,478 | B2 | 7/2019 | Kusens |
| 10,382,724 | B2 | 8/2019 | Kusens |
| 2012/0180327 | A1 | 7/2012 | Dufour |
| 2015/0206415 | A1 | 7/2015 | Wegelin et al. |
| 2016/0183864 | A1 | 6/2016 | Kusens et al. |
| 2017/0046577 | A1 | 2/2017 | Rocque et al. |
| 2018/0357380 | A1* | 12/2018 | Wang ........................ G06T 7/70 |
| 2019/0239824 | A1 | 8/2019 | Muhsin et al. |
| 2019/0306464 | A1 | 10/2019 | Clark et al. |
| 2022/0061664 | A1* | 3/2022 | Georgiev ................ G06F 40/58 |

FOREIGN PATENT DOCUMENTS

| | | | |
|---|---|---|---|
| AU | 2015229693 | B2 | 10/2016 |
| CA | 2682361 | C | 6/2013 |
| CN | 102341724 | B | 9/2013 |
| CN | 211203543 | U | 8/2020 |
| EP | 2331001 | B1 | 11/2018 |
| GB | 2581767 | A | 9/2020 |
| JP | H08781 | A | 1/1996 |
| JP | 2000285328 | A | 10/2000 |
| WO | 2015109277 | A1 | 7/2015 |
| WO | 2017040700 | A2 | 3/2017 |
| WO | 2017175462 | A1 | 10/2017 |
| WO | 2018064764 | A1 | 4/2018 |
| WO | 2019105542 | A1 | 6/2019 |
| WO | 2020198730 | A1 | 10/2020 |

* cited by examiner

1182

1184

1172

1176    1178    1180

1182

S1602

S1604

CLINICAL MONITORING DEVICE

CROSS-REFERENCE TO RELATED APPLICATIONS

This application is a U.S. National Stage Application filed under 35 U.S.C. § 371 of PCT/EP2021/072099, filed Aug. 6, 2021, and entitled "CLINICAL MONITORING DEVICE", which International Application claims priority from International Patent Application No. PCT/EP2020/080040, filed on Oct. 26, 2020. The entire contents of each of the above-identified patent applications are incorporated herein by reference.

TECHNICAL FIELD

The present disclosure relates to clinical monitoring. In particular, the disclosure relates to a clinical monitoring device. Also described are a clinical monitoring system comprising at least one such clinical monitoring device, and methods performed by or using such clinical monitoring device.

BACKGROUND

Monitoring of patient-related circumstances has become increasingly important in clinical environments. A significant health risk for patients in clinical environments is exposure to infectious material and multi-resistant pathogens. A main cause for this may be incorrect, improper or insufficient use of hand hygiene products when the situation requires. The World Health Organization proposes five essential situations of hand hygiene for clinical personnel, relating to a situation before interaction with a patient, before performing an aseptic activity, after contact with infectious material, after interaction with the patient, and after interaction with a patient environment.

To date, specially trained hygiene personnel is responsible for monitoring compliance with hygiene regulations, in many cases using a checklist on paper and a pen. Accordingly, such a compliance observation is not free from human error. Moreover, there is a bias because clinical personnel behaves differently when observed (so called "Hawthorne effect"). Since the checklist based approach is resource-intensive, it is not scalable.

Furthermore, it is of importance to monitor other patient-related circumstances such as the availability of free beds, in particular intensive care beds, or the condition of patients. Such a monitoring is commonly done manually or using bed-side patient monitoring equipment. A significant amount of manual effort has to be put into gaining an overview of a hospital-wide general situation.

SUMMARY

There is a need for clinical monitoring that allows assessing clinically relevant parameters, situations or circumstances in patient-related clinical environments.

According to a first aspect, a clinical monitoring device, in particular a patient zone monitoring device, is provided. The device comprises a first sensing unit comprising at least one first sensor configured to acquire spatial data representing spatially resolved depth information with respect to a first field of view (e.g., of at least one of the first sensing unit and the first sensor). The device further comprises a second sensing unit comprising at least one second sensor configured to acquire thermal data representing spatially resolved temperature information with respect to a second field of view (e.g., of at least one of the second sensing unit and the second sensor). The device further comprises a processing unit comprising at least one processor, the processing unit being configured to receive the spatial data from the first sensing unit and the thermal data from the second sensing unit and process at least the spatial data and the thermal data to generate scene data representing information with respect to a scene in a volume comprised in at least one of the first field of view and the second field of view.

The first sensor being configured to acquire spatial data representing spatially resolved depth information with respect to the first field of view may be considered as being synonymous to the first sensor being configured to acquire spatial data representing 3-dimensional information with respect to the first field of view.

The acquired spatial data may be raw data. The acquired thermal data may be raw data. Generating the scene data may result in a net reduction of data amount. For instance, the rate at which scene data is generated may be smaller than the rate at which at least one of the spatial data and the thermal data is generated (e.g., at least during acquisition of the spatial data).

The at least one sensor may be configured to measure a plurality of distances to different points within the field of view. The spatial data may be in the form of distance values. The spatial data may alternatively be in the form of data points, each data point having an associated 3-dimensional position in a 3-dimensional coordinate system.

The first field of view may be directed to an area specially adapted for receiving a patient bed, such as a portion of a patient room, a portion of an emergency room or a portion of an operating room. The first field of view may define a volume to which the spatial data corresponds. The first field of view may be substantially conical in shape, wherein a base of the respective view cone may be defined by a floor of a room, and wherein a tip of the cone may be defined by a position of the at least one first sensor.

The second field of view may be directed to an area specially adapted for receiving a patient bed, such as a portion of a patient room, a portion of an emergency room or a portion of an operating room. The second field of view may define a volume to which the spatial data corresponds. The second field of view may be substantially conical in shape, wherein a base of the respective view cone may be defined by a floor of a room, and wherein a tip of the cone may be defined by a position of the at least one second sensor.

The scene data may include information on at least one of presence, class and properties of one or more objects within the volume. The scene data may represent at least one of and particular all of a position, a trajectory, a volume, a surface, and a geometric footprint of objects present in the volume. For instance, it may be derivable from the scene data who and/or what is and/or has been present within the volume for how long. For the purpose of this disclosure, the term "object" generally refers to any person, animal, plant or lifeless thing. The scene data may represent information that relates to at least one of presence of at least one patient bed, presence of at least one occupied patient bed, occupation of at least one patient bed, presence of at least one clinical device, presence of at least one patient and presence of at least one person, in particular clinical personnel, in the volume. The at least one person may comprise a visitor of the patient. The information may relate to presence at least one person different from clinical personnel and different from the patient occupying the patient bed. The at least one person may alternatively or additionally be clinical personnel. The information may relate to presence of clinical personnel within the first field of view. The clinical device may comprise a bedside clinical device. The clinical device may comprise an infusion pump, an infusion holder, a vital sign monitoring device or the like.

The monitoring device may comprise a transmission/reception unit configured to receive the scene data from the processing unit and transmit the scene data over a communication network. Transmission of the scene data by the transmission/reception unit may occur in real time and/or intermittently and/or upon request and/or with a predefined time delay. The communication network may be a partly or entirely wireless communication network or a wired communication network. At least one receiving device configured to receive the scene data may be connected to the communication network. The receiving device may comprise an output unit for outputting data and/or information to a user.

Where it is noted herein that one unit, device, component or the like receives a signal or data from another unit, device, component or the like, it is to be understood that the unit, device, component or the like from which the signal or data is received is configured to send the signal or data. Furthermore, it is to be understood that the receiving unit, device, component or the like is configured to receive the signal or the data. A suitable, wired and/or wireless, transmission unit or transmission/reception unit may be provided for either or each of these purposes. The transmission/reception unit may be a radio transmission and reception unit.

The first field of view may at least partially overlap the second field of view. The first field of view may overlap the second field of view at least in the volume. Alternatively, the first field of view may overlap the second field of view only in the volume. The second field of view may be larger than the first field of view. The second field of view may cover an entire patient room or a portion of a patient room between a door and a patient bed. The first field of view may be focused on a patient bed. The second field of view may be focused on the same area as the first field of view but extend beyond this area in at least one direction.

The processing unit may be configured to determine the volume where the first field of view overlaps the second field of view. The processing unit may be configured to obtain information indicative of the volume. The processing unit may be configured to select at least one of (i) from the spatial data, a portion of the spatial data representing spatially resolved depth information with respect to the volume, and (ii) from the thermal data, a portion of the thermal data representing spatially resolved temperature information with respect to the volume. The processing unit may be configured to determine the scene data based on the at least one selected portion. The processing unit may be configured to determine the scene data based on the selected portion of one of the spatial data and the thermal data and based on the other of the spatial data and the thermal data.

The monitoring device may further comprise at least one of a mask and a lens. The at least one of the mask and the lens may be arranged such that it defines at least one of the first field of view and the second field of view. The at least one of the mask and the lens may form an outline of the at least one of the first field of view and the second field of view. The at least one of the mask and the lens may comprise or be an aperture. The processing unit may be configured to determine the volume based on information related to the at least one of the mask and the lens. This information may comprise one or more of an indication of a geometrical form of the at least one of the mask and the lens, an outline defined by the at least one of the mask and the lens, a type of the at least one of the mask and the lens and a spatial relationship between (i) the at least one of the mask and the lens and (ii) at least one of the first sensor and the second sensor.

The processing unit may be configured to generate the scene data by (i) analyzing the spatial data to detect an object present in the volume, and by (ii) comparing, based on thermal data, a temperature of one or more surface areas of the detected object with at least one predefined thermal property associated with at least one object class to classify the detected object. The comparing may include mapping the thermal data to the spatial data. The comparing may comprise overlaying the spatial data (e.g., a portion of the spatial data related to a detected object) with the thermal data (e.g., of the same object). The object class may indicate one or more of a type, a name and an identity of the object. The type of the object may be a person, a patient bed, an occupied patient bed, a medical device or an unknown object.

The processing unit may be configured to generate the scene data based upon an analysis of at least one of spatial data acquired at different times and thermal data acquired at different times. The processing unit may accordingly be configured to process currently as well as previously acquired (e.g., thermal and/or spatial) data in order to generate the scene data. The (e.g., thermal and/or spatial) data acquired at a certain point in time may be used several times for generating scene data. Generating the scene data may include tracking a position and/or orientation and/or volume of at least one object and in particular of several interacting objects over time based upon the (e.g., thermal and/or spatial) data acquired at different times.

The processing unit may be configured to generate the scene data by (i) analyzing the spatial data to detect an object present in the volume, and by (ii) comparing, based on the thermal data acquired at different times, a temporal temperature behavior of one or more surface areas of the detected object with at least one predefined thermal property associated with at least one object class to classify the detected object. The comparing may include mapping the thermal data acquired at a first point in time to the spatial data acquired at the first point in time and mapping the thermal data acquired at a second point in time to the spatial data acquired at the second point in time. The comparing may comprise overlaying the spatial data acquired at a first point in time (e.g., a portion of the spatial data related to a detected object) with the thermal data (e.g., of the same object) acquired at the first point in time and overlaying the spatial data acquired at a second point in time with the thermal data acquired at the second point in time. As noted above, the object class may indicate one or more of a type, a name and an identity of the object. The type of the object may be a person, a patient bed, an occupied patient bed, a medical device or an unknown object.

The at least one predefined thermal property may be associated with a predefined region of objects of the at least one object class. The one or more surface areas of the detected object may be comprised in an object region of the detected object, the object region corresponding to the predefined region. One may say that the at least one predefined thermal property may be a unique or characteristic thermal property of the predefined region of the objects of the at least one object class. For example, the predefined region may be a head end of an occupied patient bed and the thermal property may define that the head end exhibits a surface temperature between 20° C. and 45° C. As another example, the predefined region may be a head end of an unoccupied patient bed and the thermal property may define that the head end exhibits a surface temperature between 10° C. and 30° C. As a still further example, the predefined region may lie on a display screen of a medical device and the thermal property may define that the display screen exhibits a surface temperature between 40° C.-60° C.

The scene data may represent information regarding at least one of a temporal and a spatial relationship between at least two different objects present in the volume. One of the at least two different objects present in the volume may be an occupied patient bed and another one of the at least two different objects may be a person, wherein the scene data may represent information that relates to the person bending over the occupied patient bed.

The spatial relationship may comprise at least one of a distance between the objections, a relative movement of the objects and a partial overlap or merging of the objects in a 2-dimensional and/or in a 3-dimensional representation of the underlying scene. The temporal relationship may relate to a time period for which a certain spatial relationship exists. Furthermore, at least one of the spatial relationship and the temporal relationship may comprise information regarding a respective threshold such as a maximum or minimum distance or a maximal or minimal time period being exceeded or not. The scene data may represent the type of interaction between the two objects based on their temporal and/or spatial relationship. The type of interaction may be accompanied by a probability regarding accuracy of the type determination. For instance, the scene data may represent a scene in which clinical personnel interacts with a patient lying on a patient bed. According to another example, the scene data my represent a certain type of patient bed being present and occupied or unoccupied by a patient. According to a further example, the scene data may represent a person, in particular a person different from clinical personnel, visiting a patient lying on a patient bed.

The processing unit may be configured to generate, on the basis of the (e.g., thermal and/or spatial) data, the scene data based upon estimating the positions of at least two different objects in the volume, and based upon at least one of estimated volumes, estimated footprints and estimated surfaces of the at least two different objects. The spatial data may contain a 3-dimensional envelope surface for each object. The footprint may correspond to a projection parallel to a surface normal of a floor and/or parallel to a surface normal of a bed surface of a patient bed The monitoring device may further comprise an orientation sensor configured to acquire orientation data representing an orientation of the monitoring device. The orientation sensor may comprise one or more acceleration sensors, for example a three-axis acceleration sensor. The orientation sensor may be configured to determine the orientation of the monitoring device relative to a ceiling and/or a floor of a room in which the monitoring device is arranged. The processing unit may be configured to obtain height information indicating a distance, in particular a minimal distance, between the monitoring device and a floor. The processing unit may be configured to determine, on the basis of the orientation data and the height information, pose data indicative of a position and orientation of the monitoring device relative to the floor. The processing unit may be configured to generate the scene data further based on or under consideration of the pose data. The processing unit may be configured to determine, on the basis of the spatial data and the pose data, an estimated height level of one or more surfaces of an object present within the volume, the estimated height level being determined relative to the floor. The processing unit may be configured to generate the scene data based on the estimated height level. The processing unit may calibrate at least one of the first sensing unit and the second sensing unit based on the pose data, for example such that the at least one of the first sensing unit and the second sensing unit is configured to generate or output the (e.g., spatial or thermal) data with reference to the floor (e.g., such that the floor is used as a height or temperature reference for the data).

The processing unit may be configured to determine, on the basis of the spatial data (e.g., and the pose data), at least one of an estimated height level of a floor and an estimated height level of a bed surface of a patient bed, estimate a geometry of the bed in an empty state thereupon, and compare said expected empty bed geometry to the spatial data actually acquired. From such a comparison, presence of a patient in the bed may be determined. Said height level may serve as reference for determining height levels of other objects. An occupation status of a patient bed may be determined by comparing the estimated height level of the bed surface with a predefined height level associated with one of an unoccupied patient bed and an occupied patient bed. Additionally or alternatively, reference values may be determined in advance and/or stored in the monitoring device, such as a mounting height over a floor, a basic geometry of a patient bed present in the first field of view etc.

The transmission/reception unit may be configured to determine at least one of an ID and a distance of at least one of a clinical personnel beacon, a patient beacon, a patient bed beacon and a clinical device beacon. The processing unit may be configured to receive at least one of said ID and said distance from the transmission/reception unit and generate the scene data in addition based upon at least one of said ID and said distance. In some embodiments, the transmission/reception unit may be configured to operate using a low-energy protocol. The respective beacon may be a low-energy beacon, such as a Bluetooth beacon, in particular a Bluetooth Low Energy beacon. The transmission/reception unit may comprise a Bluetooth transceiver. The transmission/reception unit may be configured to send Bluetooth Low Energy Advertising Event signals. The transmission/reception unit may be configured to perform Bluetooth Low Energy scans. The patient beacon may contain stored information regarding at least one of a name of a patient, an ID of a patient, an ID of the patient beacon, and medical information of the patient. The clinical personnel beacon may contain stored information regarding at least one of a name of the personnel, an ID of the personnel, an ID of the clinical personnel beacon, a role of the personnel and an assignment of the personnel. In particular for anonymized applications the ID of the respective beacon may be associated with further information using an anonymization protocol. For instance, clinical personnel beacons may be randomly assigned and/or re-assigned to individual personnel on a regular basis. The patient bed beacon may contain stored information regarding a type of a patient bed such as intensive care bed, regular patient bed, obesity bed or children's bed. The clinical device beacon may contain stored information regarding a type of clinical device, a planned position or assignment of the clinical device and a status of the clinical device.

Alternatively or additionally, the processing unit may be configured to generate the scene data based upon at least one of an identity and a distance of at least one of a clinical personnel, a patient, a patient bed and a clinical device from the spatial data and/or the thermal data. An identification may be based on a comparison with stored identity data such as expected spatial and/or thermal properties. An identification may alternatively or additionally be based on determining, based upon the (e.g., spatial and/or thermal) data received by the processing unit, a color and/or a surface structure and/or an image of at least a portion of an object. Identification may be based upon using at least one of a bar code, a QR code, an information-carrying surface texture and an icon.

An ID determined using at least one beacon and/or an ID determined otherwise may be included in the scene data. For this purpose, the identity may be assigned to the respective object. The scene data may thus comprise information which relates for instance to a certain individual entering a space (e.g., the first field of view, the second field of view of the volume), a certain patient being present in a certain bed in the space, wherein said certain individual interacts with said certain patient in a certain way. The interaction may for instance be identified as treatment and/or examination and/or round visit.

The monitoring device may further comprise a third sensing unit comprising at least one passive sensor configured to generate a sensing signal responsive to an object entering or exiting a third field of view (e.g., of at least one of the third sensing unit and the passive sensor).

The third field of view may lie at least partially outside of at least one of the first field of view and the second field of view. For example, among the first field of view, the second field of view and the third field of view, only one or only both of the first field of view and the second field of view cover an area in which a patient bed is arranged or is to be arranged. The at least one of the mask and the lens mentioned above or a separate mask comprised in the monitoring device may restrict and/or define a contour or shape of the third field of view.

The processing unit may be configured to receive the sensing signal from the third sensing unit and generate the scene data further based on the sensing signal, wherein the scene data represents information with respect to a scene in both the volume and the third field of view. For instance, the sensing signal may indicate that a person enters the third field of view and the scene data may describe that the person is close to a patient bed arranged within the volume. The sensing signal may be used as a required precondition for the detection of a person within the volume.

Alternatively or additionally, the processing unit may be configured for generating a wake-up signal for at least one sensor selected from the first sensor and the second sensor, the wake-up signal causing a wake-up operation of (e.g., only) the at least one sensor. The ware-up signal may cause a wake-up operation of the processor of the processing unit. The processing unit may be configured to generate the wake-up signal responsive to the passive sensor generating the sensing signal, in particular responsive to the passive sensor detecting an object entering the third field of view.

The processing unit may be configured to generate the wake-up signal depending upon at least one of detection of an object in the third field of view by the passive sensor and reception of a sensing demand signal from the communication network. The wake-up signal may be generated in reaction to a person entering the first, second and/or third field of view. The sensing demand signal may be generated based upon a user input and/or based upon a timing signal. For instance, a demand signal may be sent in certain time intervals in order to obtain associated snapshots of the volume by operating the first and the second sensor for a time period shorter than the time interval, for instance at least 10 times shorter, at least 20 times shorter, at least 50 times shorter or at least 100 times shorter.

The monitoring device may further comprise a fourth sensing unit comprising at least one luminosity sensor configured to acquire luminosity data representing an average luminosity with respect to a fourth field of view (e.g., of at least one of the fourth sensing unit and the luminosity sensor). The luminosity sensor may be configured to detect a luminosity falling onto the monitoring device or a luminosity within a room in which the monitoring device is arranged.

The processing unit may be configured to generate the scene data further based on the luminosity data, in particular based on a temporal change in the luminosity represented by the luminosity data. The processing unit may compare the temporal change with a predefined set of changes, each being associated to a certain event (e.g., opening or closing of a door, opening or closing of a window shutter, (de-) activation of a room lighting). The event may then be included in the scene data.

The event may be used as a wake-up event to trigger activation of one or more of the other sensors of the monitoring device. The processing unit may be configured for generating a primary wake-up signal for the passive sensor, the primary wake-up signal causing a wake-up operation of (e.g., only) the passive sensor. The primary wake-up signal may cause a wake-up operation of at least one of the first sensor, the second sensor and the processor of the processing unit. The processing unit may be configured to generate the primary wake-up signal responsive to determining that a luminosity indicated by the luminosity information exceeded a predefined threshold for a predefined time, or responsive to determining presence of a wake-up event.

The wake-up operation of the respective sensor (e.g., the first sensor, the second sensor or the passive sensor) may configure the respective sensor with a higher sensor sampling rate compared with a non-zero sensor sampling rate of the respective sensor before the wake-up operation. One may say that the wake-up operation corresponds to a sampling rate increase command.

Alternatively, the wake-up operation may configure or trigger the respective sensor or the processor of the processing unit to be turned on. In this alternative, the respective sensor may be operational only in an activated state. In this alternative, the basic mode of the respective sensor may be a sleep mode.

The processing unit may be configured to generate a sleep-mode signal for a respective sensor (e.g., at least one of the first sensor, the second sensor and the passive sensor) causing the respective sensor to transition into a sleep mode. The processing unit may be configured to generate the sleep-mode signal depending upon at least one of a time period of activation of the respective sensor (e.g., at least one of the first sensor and the second sensor), a time-period of not detecting an object by the passive sensor, an availability of operational power, and a reception of a sleep demand signal from the communication network. The sleep demand signal may be generated automatically and/or based on a user input. The transition into a sleep mode may correspond to a shutdown or a turning off of the respective sensor. Alternatively, the transition into the sleep mode may configure the respective sensor with a lower sensor sampling rate than before the transition into the sleep mode.

The first sensor may be an active sensor. The first sensor may be a time-of-flight sensor. The first sensing unit may comprise a time-of-flight camera. The first sensor may be a radar sensor or a lidar sensor. The first sensor may be a millimeter wave radar sensor. The first sensor may generally be configured to determine a height profile over a 2-dimensional raster. Additionally or alternatively, the first sensor may comprise a stereoscopic camera. The first sensing unit may generally comprise several active sensors of the same type or of different types. The first sensor may be in the form of an active sensor unit comprising a time-of-flight sensor and a video camera. In this case, spatial data may be obtained based upon a correlation of a video image and acquired time-of-flight data.

The passive sensor may be an infrared sensor, in particular a passive infrared sensor, PIR. The passive sensor may comprise at least one of an infrared sensor, a brightness sensor or a piezo sensor. The passive sensor may be configured to detect at least one of infrared radiation, visible light, UV light, acoustic waves, vibrations, shocks, voices and footsteps.

In some embodiments, a second active sensor (e.g., the second sensor) may be used instead of or in addition to the passive sensor. The second active sensor may operate at a lower power than the active sensor. The second active sensor may be activated intermittently or operated permanently. The operation, in particular the wake-up operation, of the active sensor may work analogously to the case of the passive sensor. In further embodiments, in particular in case the monitoring unit is permanently connectable to an electric grid, the sensing unit may not comprise the passive sensor.

It is noted that in some variants, the monitoring device may not comprise the second sensing unit. In this case, the processing unit may be configured to determine the scene data (e.g., only) based on the spatial data. Alternatively, the monitoring device may not comprise the first sensing unit. In this case, the processing unit may be configured to determine the scene data (e.g., only) based on the thermal data. The monitoring device may comprise at least one of the first sensing unit, the second sensing unit, the third sensing unit and the fourth sensing unit. The monitoring device may comprise multiple instances of at least one of the first sensing unit, the second sensing unit, the third sensing unit and the fourth sensing unit. The monitoring device may comprise one or more further sensing units, each comprising at least one sensor configured to acquire sensor data related to the scene. The processing unit may be configured to generate the scene data based on sensor data received from one or more, in particular all sensing units comprised in the monitoring device.

One of such further sensing units may comprise one or more microphones configured to acquire sound data related to the scene. The processing unit may be configured to process the sound data to generate the scene data. Processing the sound data may involve conducting at least one of spectral analysis, voice recognition, speech recognition and sound recognition (e.g., recognition of a warning signal) to classify an object emitting sound (and, e.g., enrich the scene data with information on a text spoken by a person in the scene). In case the further sensing unit comprises a plurality of microphones, processing the sound data may comprise comparing sound signals of the plurality of microphones to localize the object emitting sound (e.g., using triangulation).

Another of such further sensing units may comprise a gas sensor, for example a carbon dioxide sensor or a hydrogen sensor, configured to acquire gas data related to the scene. The gas sensor may be a volatile organic compound, VOC, sensor. The processing unit may be configured to determine, based on the gas data, at least one of presence of a person, a dangerous level of carbon dioxide within a room in which the monitoring device is arranged, and an occurrence of or a type of a disease of a patient. This information may trigger (e.g., after being transmitted via the network) control of ventilation of the room in which the monitoring device is arranged or activation of fire distinguishers within the room in which the monitoring device is arranged. Doctors may be informed of the occurrence or type of the disease.

The monitoring device may comprise an energy storage unit configured to provide operational power allowing the monitoring device to be fully operational independently of an electricity grid. The monitoring device may be an autarkic monitoring device. The energy storage unit may comprise at least one battery. Alternatively or additionally the energy storage unit may comprise a capacitor, a supercapacitor, or a hydrogen tank and a fuel cell. The energy storage unit may be configured to store energy which allows operation of the monitoring device, in particular under normal operating conditions, for at least 1 months, at least 3 months, least 6 months or at least 1 year if fully charged/loaded.

The monitoring device may comprise an energy harvesting unit configured to harvest energy from an indoor environment. The energy harvesting unit may be configured to charge the energy storage unit. The energy harvesting device may comprise an indoor solar cell. Alternatively or additionally the energy harvesting device may comprise a thermoelectric device or an acousto-electric device. In some embodiments, the energy harvesting unit may be configured to harvest energy from a magnetic field, in particular from a magnet field of an inductive charging system. In such embodiments, the energy harvesting unit may be considered a power supply unit configured to be used as receiver in a wireless power supply network.

The processing unit may be configured to generate the scene data such that it represents information regarding at least one of and in particular all of the following: presence of an empty patient bed; presence of an occupied patient bed; presence of an empty patient bed of a certain type; presence of an occupied patient bed of a certain type; presence of a clinical device; presence of a clinical device of a certain type; presence of at least one person; presence and identity of at least one person; presence of clinical personnel; presence and identity of clinical personnel; interaction between clinical personnel and a patient; interaction between clinical personnel and a patient zone; presence of clinical personnel before an interaction with a patient; presence of clinical personnel after interaction with a patient; presence of clinical personnel after interaction with a patient zone; absence of clinical personnel after interaction with the patient; absence of clinical personnel after interaction with the patient zone; presence of clinical personnel before an aseptic activity; presence of clinical personnel after an aseptic activity; presence of a patient in a certain acute condition; amount of movement of a patient during a certain time period; and presence of a patient who has fallen out of a bed. The scene data may comprise some of all of the mentioned information associated with a respective time of occurrence and/or time period of being present.

The monitoring device may have a maximum extension in a direction of maximum extension of not more than 50 cm, not more than 30 cm, not more than 20 cm or not more than 10 cm.

The monitoring device may comprise one or more features described herein below with reference to the tenth aspect. The monitoring device may comprise a housing with a mounting unit (also referred to as "retainer" herein). The housing may house at least one of the first sensing unit, the second sensing unit, the third sensing unit, the fourth sensing unit, the further sensing unit(s), the processing unit and the transmission/reception unit. The mounting unit may be configured to be affixed to at least one of a ceiling and a wall. The mounting unit may comprise through-holes for attaching the monitoring device using screws, nails or rivets. Alternatively or additionally, the mounting unit may comprise at least one magnet or at least one ferromagnetic element configured to be magnetically removably connected to a mounting.

According to a second aspect, a clinical method, in particular a patient zone monitoring method, is provided. The clinical method may comprise using a monitoring device according to the disclosure. The clinical method may comprise: acquiring the spatial data described herein; optionally acquiring the thermal data described herein; and processing the spatial data and optionally the thermal data to generate the scene data. The method may be performed by the processing unit described herein. The method may further comprise method steps corresponding to the functionalities of the monitoring device described above.

The method may comprise processing the spatial data (and, e.g., the thermal data) in order to generate scene data representing information with respect to a scene in the first field of view of the sensing unit, wherein the scene data represents information that relates to at least one of presence of at least one patient bed, occupation of at least one patient bed, presence of at least one clinical device, presence of at least one patient, and presence of at least one person, in particular clinical personnel, in the field of view of the sensing unit. The method may comprise transmitting the scene data over a communication network.

According to a third aspect, a clinical method, in particular a patient zone monitoring method, is provided. This clinical method may comprise using a receiving device as mentioned above. The method comprises receiving the scene data described herein, in particular scene data generated using a monitoring device or a clinical method according to the disclosure, over a communication network. The method may further comprise method steps corresponding to the functionalities of the monitoring device and/or the receiving device described above. The scene data may represent information that relates to at least one of presence of a patient bed, occupation of a patient bed, presence of at least one clinical device, presence of a patient and presence of clinical personnel in the field of view of the sensing unit.

According to a fourth aspect, a clinical monitoring system is provided. The clinical monitoring system comprises at least one monitoring device according to the disclosure. Furthermore, the clinical monitoring system comprises a monitoring unit comprising at least one processor, the monitoring unit being configured to receive the scene data from the monitoring device and process the scene data.

The monitoring system may comprise a server comprising the monitoring unit. The server may be a dedicated server. The server may be a distributed server. The server may be a cloud server. The server may be a local server.

Alternatively, the monitoring system may comprise a terminal comprising the monitoring unit. The terminal may be a mobile terminal. The terminal may be a personal third-party device such as a smartphone, a tablet computer, a desktop computer, a laptop or a handheld device.

The monitoring system may comprise a server and one or more terminals, in particular mobile terminals. The monitoring unit may be implemented as distributed unit. In other embodiments, the terminals function merely as user interfaces and the monitoring unit is entirely provided on the server.

In some embodiments, the monitoring device is arranged in an area of concern. The monitoring system may then further comprise at least one portable device and at least one hygiene dispenser arranged in the area of concern. Furthermore, the monitoring system may comprise at least one treatment detection unit configured to detect a disinfection treatment performed with the hygiene dispenser, identify the portable device, and generate treatment data representing information regarding the detected treatment and the identified portable device. The monitoring unit may further be configured to receive the treatment data from the treatment detection unit and determine a hygiene status based upon the treatment data and the scene data, and assign the hygiene status to the portable device.

The area of concern may contain at least one of a patient room, an emergency room and an operation room. The area of concern may generally contain a region or area around and including an area designated for a patient bed.

The portable device may be a wearable badge. The portable device may be a smart card, a beacon, a transponder, a dongle, a smartphone, a smartwatch, a head-mounted display or another device suitable for being carried by a person and for being automatically identified. The portable device may be configured to function based on a low-energy communication protocol. Alternatively or additionally the portable device may carry an identifier such as a bar code, a QR code, a printed label, an icon, a passive RFID tag, an active RFID tag and/or a magnetic strip. The portable device may comprise a card holder configured to removable hold an identification card and to identify an identification card. The portable device, in particular in the form of a card holder, may further comprise at least one sensor configured to determine a type of the identification card and/or an ID assigned to the identification card.

The portable device may comprise a movement sensor configured to acquire movement data, in particular at least one of a step counter and an acceleration sensor. The movement data may comprise a trajectory, a trajectory associated with times, velocity data, acceleration data, a distance traveled and/or a number of steps. The monitoring device may be configured to communicate with the portable device and to receive from the portable device the movement data. The processing unit of the monitoring device may be configured to generate the scene data based upon the movement data received from the portable device. The monitoring device may take into account movement of the portable device and in particular movement of clinical personnel carrying the portable device, the movement having taken place outside of at least one of the first field of view, the second field of view, the third field of view and the fourth field of view, in particular outside the first and the second field of view.

The dispenser may be arranged at a location in proximity of a patient bed accessible by clinical personnel for hand sanitizing prior to, during, or after interaction with the patient.

The hygiene status may depend upon a time since the last disinfection treatment. The hygiene status may further depend upon the situation detected, i.e. the scene represented by the scene data. For instance, the hygiene status may be acceptable for a certain time period after the disinfection treatment, allowing the clinical personnel to walk from a hygiene dispenser into a patient zone. This time period may be in the order of seconds. The hygiene status may be changed to unacceptable after interaction with a patient. The hygiene status may then only be set back to acceptable after another disinfection treatment has been performed. The hygiene status may be set depending upon at least one or all of the above-mentioned five hygiene situations and a corresponding disinfection event. These situations are called "five moments of hand hygiene" by the WHO. Merely as an example, clinical personnel is required to sanitize hands before an aseptic activity. Hence, if the scene data indicates that an aseptic activity is being performed, the hygiene status may only acceptable if the last disinfection has been performed not longer ago than a certain threshold time, and may in addition only be acceptable if no other hygiene-relevant activity has been performed in the meantime.

The portable device may be configured to receive the hygiene status from the monitoring unit and to generate at least one perceptible output indicative of the hygiene status. The perceptible output may comprise at least one of an audio signal, a haptic signal, a visual signal, a vibration signal, an image, an animation and a light color.

The monitoring system may further comprise at least one output device arranged in the area of concern, the output device being configured to receive the hygiene status from the monitoring unit and to generate at least one perceptible output indicative of the hygiene status. The perceptible output may comprise at least one of an audio signal, a haptic signal, a visual signal, a vibration signal, an image, an animation and a light color. The output device may comprise a display device and/or a speaker.

The monitoring unit may be configured to modify the scene data received from the monitoring device such that it represents information regarding at least one of the following: presence of an empty patient bed; presence of an occupied patient bed; presence of an empty patient bed of a certain type; presence of an occupied patient bed of a certain type; presence of a clinical device; presence of a clinical device of a certain type; presence of at least one person; presence and identity of at least one person; presence of clinical personnel; presence and identity of clinical personnel; interaction between clinical personnel and a patient; interaction between clinical personnel and a patient zone; presence of clinical personnel before an interaction with a patient; presence of clinical personnel after interaction with a patient; presence of clinical personnel after interaction with a patient zone; absence of clinical personnel after interaction with the patient; absence of clinical personnel after interaction with the patient zone; presence of clinical personnel before an aseptic activity; presence of clinical personnel after an aseptic activity; presence of a patient in a certain acute condition; amount of movement of a patient during a certain time period; and presence of a patient who has fallen out of a bed. In particular, said information may be determined and supplemented to the scene data by the monitoring device itself, by the monitoring unit of the monitoring system, or by both. In some embodiments, the monitoring device includes some of the mentioned information in the scene data and the monitoring unit supplements some further information to the scene data. The monitoring unit may derive said information based upon comparison of scene data from several monitoring devices and/or based upon comparison of current scene data with stored scene data and/or with data stored in data base. A first scene interpretation step may be performed by the monitoring device, and a second scene interpretation step may be performed based thereon by the monitoring unit.

The monitoring unit may be configured to determine, on the basis of the scene data, that clinical personnel is in at least one of the following situations: before interaction with a patient, before an aseptic activity, after contact to infectious material, after interaction with a patient, and after interaction with a patient zone. The monitoring unit may further by configured to determine, on the basis of the treatment data, whether or not clinical personnel has sanitized hands before or in said situation. In some embodiments, the monitoring unit is configured to recognize only one or only some of the mentioned situations. In other embodiments the monitoring unit is configured to distinguish between each of the mentioned situations.

The clinical monitoring system according to the disclosure may comprise a plurality of monitoring devices, each according to the disclosure, the monitoring devices being arranged in different areas of concern. The monitoring unit may be configured to receive scene data from each of the plurality of monitoring devices, and generate, on the basis of the received scene data, bed occupation data representing information regarding presence and occupation state of different patient beds present in the different areas of concern. Furthermore, the monitoring system may comprise an output unit configured to receive the bed occupation data from the monitoring unit and output the bed occupation data to a user.

The different areas of concern may contain different patient rooms and/or one or more emergency rooms and/or one or more operating rooms. Generally speaking, the different areas of concern correspond to different regions within a clinical environment designated for placing a patient bed therein.

The plurality of monitoring devices and the monitoring unit may be connected over the communication network. The output unit may be connected to the communication network.

The output unit may comprise a terminal as discussed above. The output unit may be an input/output unit configured to receive input from a user in addition to outputting the bed occupation data to a user.

The bed occupation data may be visual data and/or tabular data. The occupation data may correspond to an occupation plan of a plurality of different patient beds, in some embodiments, patient beds of different types. The occupation data may comprise stratified data corresponding to different types of patient beds and/or patient beds in different clinical sections and/or patient beds occupied by different types of patients.

The output unit may be part of a user interface configured to receive user input. The monitoring unit may be configured to generate the bed occupation data based upon the user input such that the output of the bed occupation data is interactive. The user interface may comprise any suitable input device such as a keyboard, a mouse, a joystick, a trackball, a touch-sensitive device, a touch screen, a speech recognition system, a gesture recognition system etc.

The monitoring unit may be configured to generate, on the basis of the scene data, patient monitoring data. The monitoring system may further comprise an output unit configured to receive the patient monitoring data from the monitoring unit and output the patient monitoring data to a user.

The patient monitoring data may represent information regarding at least one vital function of the patient. The patient monitoring data may represent information regarding a position and/or posture of the patient. The patient monitoring data may alternatively or additionally represent information regarding a time the patient is in a certain position and/or posture. The patient monitoring data may represent information regarding compliance with a patient accommodation protocol.

The output unit may be part of a user interface configured to receive user input. The monitoring unit may be configured to generate the patient monitoring data based upon the user input such that the output of the user monitoring data is interactive. The user interface may comprise any suitable input device such as a keyboard, a mouse, a joystick, a trackball, a touch-sensitive device, a touch screen, a speech recognition system, a gesture recognition system etc.

At least one of the processing unit of the monitoring device and the monitoring unit may be configured to evaluate a temporal evolution of height information of a region associated with a patient with respect to a region associated with a surface of a patient bed, and to determine an amount of patient movement over time based upon said temporal evolution. The region may be associated with a certain body part of the user. The movement of the patient may be analyzed in order to identify occurrence of an acute condition of the patient, such as the patient going into shock and/or suffering an attack or a seizure. For this purpose, determined movement patterns may be compared to stored information regarding typical movement patterns indicative of certain medical conditions.

At least one of processing unit of the monitoring device and the monitoring unit may be configured for generating at least one alarm in case of occurrence of an acute condition of the patient. The alarm may be received by the output device. The output device may output the alarm.

At least one of the processing unit of the monitoring device and the monitoring unit may be configured to determine a breathing rate by tracking movement of the patient and in particular of an area associated with a chest of a patient over time.

The monitoring unit may be configured to generate the patient monitoring data on the basis of the determined breathing rate. Spatial data may be analyzed in order to determine and/or track a portion of the detected object estimated to correspond to the chest of the patient. In case periodic movement of said portion is detected, a period of the periodic movement may be used as estimate for the breathing rate of the patient.

The patient monitoring data may represent information regarding a risk for pressure sores. A risk for pressure sores may for example be determined based upon comparison of an amount of movement of the patient over time with at least one threshold value. For instance, if the patient monitoring data indicates that the patient has not turned over for more than a predetermined time, an alarm may be generated indicating an increased risk for pressure sores.

According to a fifth aspect, a clinical method using a monitoring system according to the disclosure generally comprises generating, with the monitoring device, scene data; receiving, with the monitoring unit, the scene data; and processing, with the monitoring unit, the scene data.

According to a sixth aspect, a clinical method for monitoring hygiene compliance using a monitoring system according to the disclosure is provided. The clinical method may comprise providing clinical personnel with the portable device and detecting, with the treatment detection unit, a disinfection treatment performed by the clinical personnel due to identification of the portable device. The method may comprise generating, with the treatment detection unit, treatment data representing information regarding the detected treatment and the identified portable device. The method may comprise generating, with the monitoring device, scene data relating to the area of concern. Furthermore, the method may comprise receiving, with the monitoring unit, the treatment data and the scene data. The method may further comprise determining, with the monitoring unit, a hygiene status based upon the treatment data and the scene data. The method may also comprise assigning, with the monitoring unit, the hygiene status to the portable device.

The method may further comprise determining, on the basis of the scene data, that clinical personnel is in at least one of the following situations: before interaction with a patient, before an aseptic activity, after contact to infectious material, after interaction with a patient, and after interaction with a patient zone. Furthermore, the method may comprise determining, on the basis of the treatment data, whether or not clinical personnel has sanitized hands before or in said situation.

According to a seventh aspect, a clinical method for monitoring availability and occupation of patient beds in a medical facility using a monitoring system according to the disclosure is provided. The clinical method may comprise generating, with the plurality of monitoring devices, respective scene data relating to the different areas of concern. The clinical method may further comprise receiving, with the monitoring unit, the scene data from each of the plurality of monitoring devices. Furthermore, the clinical method may comprise generating, with the monitoring unit, bed occupation data representing information regarding presence and occupation state of different patient beds present in the different areas of concern. The clinical method may comprise receiving, with the output unit, the bed occupation data from the monitoring unit. The clinical method may also comprise outputting, with the output unit, the bed occupation data to a user.

According to an eighth aspect, a clinical method for patient monitoring using a monitoring system according to the disclosure is provided. The clinical method may comprise generating, with the monitoring device, scene data. Furthermore, the clinical method may comprise receiving, with the monitoring unit, the scene data. The clinical method may further comprise generating, with the monitoring unit, patient monitoring data on the basis of the scene data. The clinical method may comprise receiving, with the output unit, the patient monitoring data. The clinical method may also comprise outputting, with the output unit, the patient monitoring data.

According to a ninth aspect, a clinical monitoring device and/or clinical monitoring system, in particular a patient zone monitoring device and/or a patient zone monitoring system, is provided. The monitoring device and/or monitoring system comprises a sensing unit comprising at least one sensor configured to acquire spatial data (e.g.,) representing 3-dimensional information with respect to a first field of view of the sensing unit). The monitoring device and/or monitoring system further comprises a processing unit comprising at least one processor, the processing unit being configured to receive the spatial data from the sensing unit (and, e.g., thermal data from a second sensing unit comprised in the monitoring device and/or monitoring system) and process the spatial data (and, e.g., the thermal data) in order to generate scene data. The scene data may represent information with respect to a scene in the first field of view of the sensing unit, wherein the scene data represents information that relates to at least one of presence of at least one patient bed, occupation of at least one patient bed, presence of at least one clinical device, presence of at least one patient and presence of at least one person, in particular clinical personnel, in the first field of view of the sensing unit. The sensing unit may be configured to send the spatial data to the processing unit over a communication network.

Where reference is made to the processing unit of a clinical monitoring device in the context of the previous aspects, it is to be understood that alternatively or in addition a processing unit implementing the same functions and/or having the same features may be used which receives the sensor data (e.g., the data from at least one of the first sensor, the second sensor, the passive sensor, the luminosity sensor and the orientation sensor) over a communication network. The processing of the spatial data and the thermal data may then be performed outside of the clinical monitoring device described above (e.g., at a remote site spaced apart from a patient room). In these cases, the monitoring device according to one or more of the above aspects may not comprise a processing unit with the described features, but instead a monitoring system may comprise the described monitoring device without the described processing unit, a communication network, and a processing unit configured as described for the processing unit of the above described monitoring device, said processing unit being configured to receive the sensor data (e.g., the spatial data and the thermal data) from the communication network and process it in order to generate scene data.

According to a tenth aspect, a clinical monitoring device, in particular a patient zone monitoring device is provided. The clinical monitoring device comprises a housing having a first side. The clinical monitoring device comprises at least one sensor arranged at (e.g., on top of or inside of) the first side of the housing.

The clinical monitoring device of the tenth aspect may comprise one or more features of the monitoring device according to the first aspect. The monitoring device of the tenth aspect may comprise at least one of the first sensing unit, the second sensing unit, the third sensing unit, the fourth sensing unit, the further sensing unit(s), the orientation sensor, the mask, the lens and the processing unit described herein. The at least one sensor arranged at the first side of the housing may be comprised in the first sensing unit, the second sensing unit, the third sensing unit, the fourth sensing unit or the further sensing unit described herein. The at least one sensor arranged at the first side of the housing may be at least one of the first sensor, the second sensor, the passive sensor and the luminance sensor described herein. The housing may house at least one of the first sensing unit, the second sensing unit, the third sensing unit and the fourth sensing unit described herein. The housing may house the processing unit described herein. The housing may house the transmission/reception unit described herein. The housing may house the further sensing unit(s) described herein. The housing may define an outer surface of the monitoring device.

The monitoring device of the tenth aspect may comprise a wireless data transmission unit (e.g., the transmission/reception unit). The wireless data transmission unit may be arranged within the housing or on an outside of the housing. The monitoring device may further comprise a processor (e.g., the processor of the processing unit described herein). The processor may be arranged within the housing and electrically connected to the at least one sensor and the wireless data transmission unit. Alternatively, the processor may be arranged on an outside of the housing.

The monitoring device of the tenth aspect comprises a retainer. The retainer comprises a coupling portion and a holding portion.

The coupling portion may be configured to be coupled to at least one of a stationary mounting, a ceiling and a wall. The coupling portion may comprise or consist of an overall flat surface configured to face the at least one of the mounting, the ceiling or the wall.

The holding portion is holding the housing (e.g., configured to hold the housing). The holding portion is configured to hold the housing such that the housing is rotatable around a first rotation axis. The holding portion may be referred to as a gripper or a clamp.

The first side of the housing may face away from the coupling portion. The holding portion may be configured to hold the housing such that the only possible relative movement between the housing and the holding portion is a rotation around the first rotation axis. The housing may be rotatably supported by the holding portion.

The housing may comprise an opening within the first side of the housing. The at least one sensor may be arranged within the housing and adjacent to the opening such that a field of view of the at least one sensor extends through the opening to an exterior of the housing.

The housing may comprise an outer housing surface. The outer housing surface may comprise a cylindrical surface portion having a cylinder axis. The cylinder axis may coincide with the first rotation axis. The holding portion may comprise a contact surface matching the cylindrical surface portion. The contact surface may be in contact with the cylindrical surface as long as the retainer is holding the housing.

The holding portion may comprise one or more retaining members extending circumferentially relative to the cylindrical surface portion. The one or more retaining members may be configured to prevent (e.g., unwanted) removal of the housing from the retainer. The one or more retaining members may block a translational movement of the housing away from the retainer. The one or more retaining members may form a claw holding the housing. The holding portion may comprise two retaining members extending in opposite directions. A distance between a distal end of each of the two retaining members may be smaller than a diameter of the cylindrical surface portion.

Each of the one or more retaining members may extend along an axis parallel to the first rotation axis. Each of the one or more retaining members may be a lip or an elongate flap.

The holding portion may be configured to hold the housing such that the housing is rotatable around the first rotation axis up to a predefined rotation angle (e.g., in one or both rotational directions). The predefined rotation angle may be ≤60°, in particular ≤50°, for example ≤45° (e.g., in each rotational direction, starting from an initial rotation angle). The holding portion may be configured to hold the housing such that the housing is rotatable around the first rotation axis within a predefined range of rotation angles. The predefined range may be 0°-120°, for example 0°-100°, in particular 0°-90°. The predefined rotation angle may be a maximum or minimum angle of the predefined range of rotation angles (e.g., 0° or 90° in case of the range of 0°-90°.

The cylindrical surface portion may comprise a first recess. At least one of the retaining members may be configured to snap into the recess upon the housing being rotated (e.g., by the predefined rotation angle).

The holding portion may comprise a locking member and the housing may comprise a second recess matching the locking member. Alternatively, the housing may comprise the locking member and the holding portion may comprise the second recess. The locking member and the second recess may be configured to couple to one another such that a relative translational movement between the housing and the holding portion along the first rotation axis is blocked.

The device may further comprise at least one orientation sensor (e.g., the orientation sensor described for the first aspect). The orientation sensor may be configured to acquire orientation data representing an orientation of the housing. The orientation may be an orientation relative to at least one of the retainer and a direction of the earth's gravity. The orientation sensor may be a rotation sensor configured to measure a rotation angle between the housing and the retainer. The orientation sensor may be a two-axis or a three-axis acceleration sensor.

The retainer (also referred to as "mounting unit" herein) may be configured to be affixed to at least one of a ceiling and a wall. The retainer may comprise through-holes for attaching the monitoring device using screws, nails or rivets.

The coupling portion may be configured to be coupled to the mounting, for example in a predefined relative orientation between the mounting and the retainer. The coupling portion may be configured to be coupled to the mounting in only one or only two predefined relative orientations between the mounting and the retainer.

The coupling portion may comprise at least one first coupling element matching at least one second coupling element of the mounting such that the first coupling element and the second coupling element form a magnetic coupling. At least one of the first coupling element and the second coupling element may comprise a magnet or a ferromagnetic element. For example, the retainer comprises at least one magnet or at least one ferromagnetic element configured to be magnetically removably connected to the mounting.

The monitoring device may have a maximum extension in a direction of maximum extension of not more than 50 cm, not more than 30 cm, not more than 20 cm or not more than 10 cm.

According to an eleventh aspect, a system comprising the clinical monitoring device of the tenth aspect is provided. The system further comprises the mounting. The mounting may be configured to be attached to a wall or a ceiling of a room. The mounting plate may be configured to removably coupled to the retainer.

According to a twelfth aspect, a system comprising the device of the tenth aspect or the system of the eleventh aspect is provided. The system of the twelfth aspect further comprises an alignment apparatus, wherein the alignment apparatus is configured to project a light pattern onto a ceiling or wall informing an installer where to attach at least one of the retainer and the mounting to the wall or the ceiling. The alignment apparatus may comprise a laser-emitting unit configured to project the light pattern. The alignment apparatus may be configured to project the light pattern in a known spatial direction relative to at least one of a floor on which the alignment apparatus is placed and the earth's gravity. The alignment apparatus may be configured to be placed on the floor next to a patient bed and project the light pattern to a predefined position on the ceiling relative to the patient bed. The predefined position may be selected such that the medical device, when arranged at the position, can capture the patient bed with the at least one sensor.

According to a thirteenth aspect, a mounting tool for use with the clinical monitoring device of the tenth aspect or the system of the eleventh aspect or the system of the twelfth aspect is provided. The mounting tool comprises a holder configured to removably hold the clinical monitoring device. The mounting tool further comprises a connector connected (e.g., coupled or movably attached) to the holder. The mounting tool comprises an elongate rod having a first end and an opposite second end, wherein the first end is fixed (e.g., relative) to the connector. The second end is configured to be grabbed by a user to move the holder with the device and couple the device in the holder to the mounting.

The holder may be configured to be rotatable relative to the rod (e.g., at least or only) around a second rotation axis. The holder may be configured to be rotatable relative to the connector around the second rotation axis. The connector may be fixed (e.g., relative) to the elongate rod. The second rotation axis may be perpendicular to at least one of a longitudinal axis of the rod, the first rotation axis and the cylinder axis.

The holder may be configured to hold the device such that the coupling portion is oriented towards the sky. The holder may be configured to hold the device such that the coupling portion is oriented towards the sky, irrespective of a rotation of the rod relative to the holder around the second rotation axis (e.g., at least within a predefined range of rotation angles between the rod and the holder around the second rotation axis).

The holder may have an inner surface portion matching an outer surface portion of at least one of the retainer and the housing. The inner surface portion may be configured to contact the outer surface portion of the at least one of the housing and the retainer when the holder is holding the monitoring device.

The holder may be configured such that the second rotation axis is arranged at (e.g., extends across) an open end of the holder. The holder may be configured such that the device is to be inserted into the open end for being held by or in the holder.

According to a fourteenth aspect, a method of arranging a clinical monitoring device in a room is provided. The room may be a room of a hospital. The method comprises using the mounting tool of the thirteenth aspect to arrange the device of the tenth aspect in the room. The method may comprise providing the system according to the eleventh aspect, wherein the mounting is attached to a wall or a ceiling of the room. The method may comprise placing the device in the holder of the mounting tool. The method may comprise grabbing the second end of the elongate rod and moving the elongate rod such that the coupling portion couples to the mounting. The method may comprise providing a preferred rotation angle between the housing and the holding portion with respect to the first rotation axis, before moving the elongate rod such that the coupling portion couples to the mounting. The preferred rotation angle may be provided by rotating the housing relative to the retainer around the first rotation axis.

According to a fifteenth aspect, a method of arranging a mounting for or a retainer of a clinical monitoring device in a room is provided. The method comprises using the alignment apparatus of the system of the twelfth aspect to project a light pattern onto the wall or the ceiling of the room. The method further comprises attaching the mounting or the retainer to the wall or the ceiling of the room at a location indicated by the projected light pattern. The method of the fifteenth aspect may be combined with the method of the fourteenth aspect.

BRIEF DESCRIPTION OF THE DRAWINGS

In the following, embodiments of the present disclosure are described with reference to the drawings, wherein.

DETAILED DESCRIPTION

Figure 1:
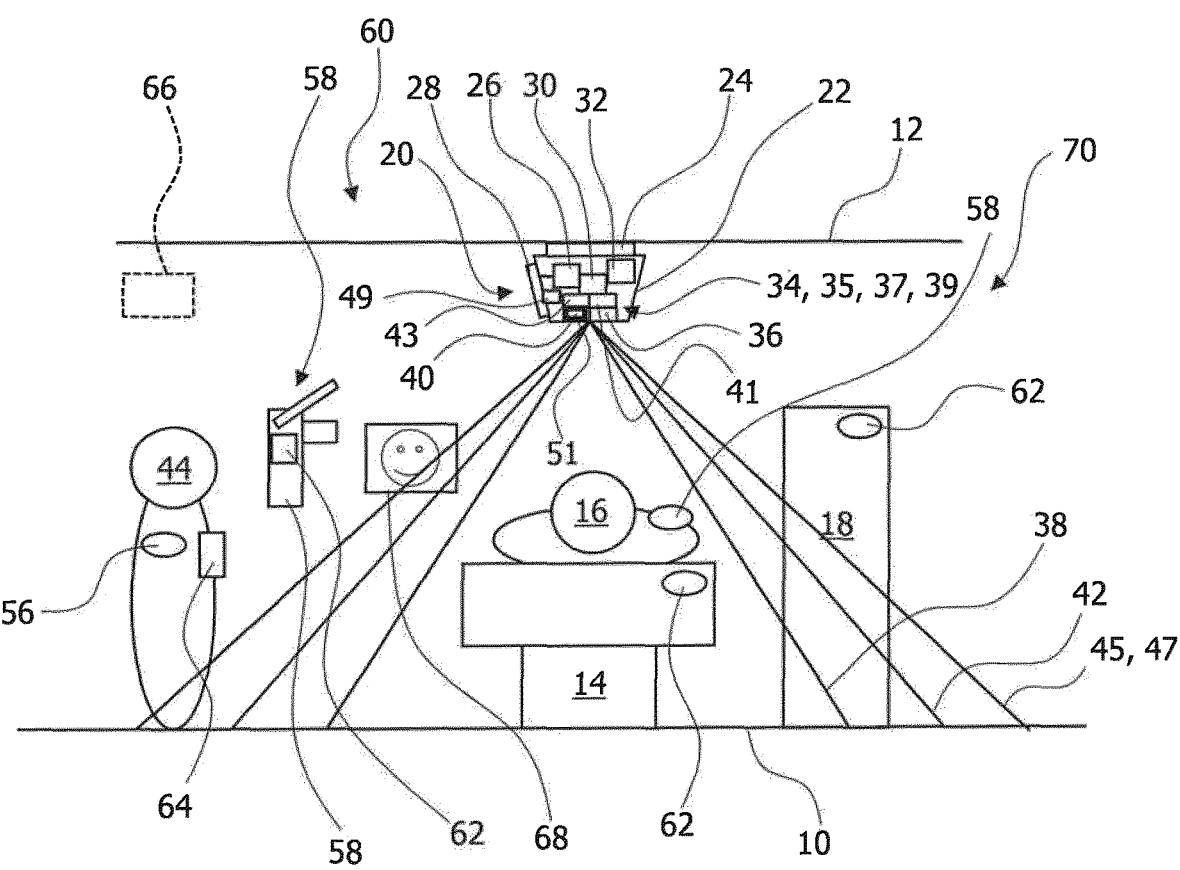
FIG. 1 shows a schematic drawing of a portion of a patient room equipped with a monitoring device.

In the following description, exemplary embodiments of a clinical monitoring device, a clinical monitoring system and a clinical monitoring method will be explained with reference to the drawings. The same reference numerals will be used to denote the same or similar structural features or method steps.

FIG. 1 shows a schematic drawing of a portion of a patient room. The patient room may be located in a hospital or another clinical or medical facility. The shown patient room merely serves exemplary purposes. An emergency room, an operating room etc. are likewise conceivable according to the disclosure.

The patient room has a floor 10 and a ceiling 12. A patient bed 14 is positioned in the patient room. A patient 16 is occupying the patient bed. A clinical device 18 such as an infusion pump or a vital function monitor is arranged next to the patient bed 14. A region around the patient 14 may be considered a patient zone. For instance, the patient bed 14, the patient 16 and the clinical device 18 are present in the patient zone. The patient zone is in particular a region which indicates possible interaction between an object entering and/or present in the patient zone and the patient 14 which is relevant with respect to hygiene.

The patient room is equipped with a clinical monitoring device 20. The monitoring device 20 comprises a housing 22 with a mounting unit 24. The mounting unit 24 is configured to mount the monitoring device 20 to a wall or a ceiling. In the present case, the monitoring device 20 is mounted on the ceiling 12 of the patient room above the patient bed 14. The housing 22 houses the components of the monitoring device 20 which will be described in the following.

The monitoring device 20 comprises an energy storage unit 26. The energy storage unit 26 may comprise a chargeable battery or another suitable energy storing device or medium as noted above. The energy storage unit 26 may be connected to all components of the monitoring device 20 which require electric energy. Due to the energy storage unit 26, the monitoring device 20 may be autarkic. The monitoring device 20 can operate independently from an electric grid. In other embodiments, the monitoring device 20 may be implemented without the energy storage unit 26 and may instead be connected to an electric grid. The monitoring device 20 may be connectable to an electric grid for charging the energy storage unit 26. In other embodiments, the energy storage unit 26 may comprise at least one removable energy storage medium which can be exchanged and/or charged in a state removed from the monitoring device 20.

The monitoring device 20 may comprise an energy harvesting unit 28, which is merely optional. The energy harvesting unit 28 may be connected to the energy storage unit 26 and configured to charge the energy storage unit 26. The energy harvesting unit 28 may for instance comprise a solar cell panel attached to an outside of the housing 22 for harvesting ambient light.

The monitoring device 20 comprises a processing unit 30 comprising a processor and a data storage medium. The processing unit 30 may comprise one or several microprocessors. The processing unit 30 may comprise analog electrical circuits and components. In the shown embodiment, the processing unit 30 is generally configured to serve as a controller of the monitoring device 20. The processing unit 30 may control the electrically addressable components of the monitoring device 20.

The monitoring device 20 further comprises a transmission/reception unit 32. The transmission/reception unit 32 is configured to send data to and receive data from a communication network 100 discussed below. In the present case, the transmission/reception unit 32 is configured for wireless operation. The transmission/reception 32 unit is configured to operate using a low-energy protocol.

The monitoring device 20 comprises a first sensing unit 34. The first sensing unit 34 comprises a first (e.g., active) sensor 36 with a first field of view 38. The monitoring device 20 comprises a second sensing unit 35 comprising a second sensor 40 with a second field of view 42. The monitoring device 20 comprises a third sensing unit 37 comprising a passive sensor 43 with a third field of view 45. The monitoring device comprises a fourth sensing unit 39 comprising a luminosity sensor 41 with a fourth field of view 47.

The first sensor 36 is a time-of-flight sensor. The first sensor 36 is configured to acquire spatial data representing 3-dimensional information with respect to the first field of view 38. The spatial data may be time-of-flight raw data. The spatial data may also be pre-processed and be in the form of a height profile over a 2-dimensional grid. Said 2-dimensional grid may be laid over and/or arranged parallel to a floor, in particular a floor of the patient room and/or a floor on which the patient bed 14 is placed.

The second sensor 40 is configured to acquire spatially resolved temperature information. The second sensor 40 may be a thermal imaging camera or an array of temperature irradiation sensors.

The passive sensor 43 is an infrared sensor. The third field of view 42 is larger than the first field of view 38. The first field of view 38 and the second field of view 42 are both focused on the patient bed 14 and the patient 16 occupying the patient bed 14. The fields of view 38, 42 overlap. The third field of view 42 extends farther away from the patient bed 14 than the first field of view 38.

The first field of view 38 and/or the second field of view may correspond to and/or may be focused onto the patient zone associated with the patient 14. Thus, an object entering and/or present in at least one of the fields of view 38, 42 may be considered entering and/or present in the patient zone.

The luminosity sensor 41 may be configured to detect an average intensity of light emitted or reflected from surfaces within the fourth field of view 47. The luminosity sensor 41 may be configured to detect an average luminosity within the patient room.

The monitoring device 20 may be arranged and/or the sensing unit(s) 34, 35, 37, 39 may be configured such that the first field of view 38 and the second field of view 42 are at least partly directed to a floor next to the patient bed 14. This allows determining a floor level from the spatial data, for instance using an appropriate numerical data fit routine for finding a 2-dimensional flat surface corresponding to a floor level. Height values of objects present in the first field of view 38 can then be determined with respect to the floor level.

The specific construction of the sensing unit 34 shown in this embodiment relates to one possible example. As noted above, other sensors may be used instead. Furthermore, one or more of the sensors may be omitted.

In the present case, the processing unit 30 is configured to perform a wake-up of the first and the second sensor 36, 40 depending upon at least one detection of an object in the third field of view 45 by the passive sensor 43. For instance, if clinical personnel 44 enters the patient room and steps within the third field of view 45, entrance of the clinical personnel 44 is detected by the passive sensor 43. The passive sensor 43 then generates a detection signal. The processing unit 30 determines, based upon the detection signal, that an object has entered the third field of view 45. The processing unit 30 then generates a wake-up signal for the first sensor 36 and the second sensor 40. Upon receiving the wake-up signal, the first sensor 36 and the second sensor 40 transition into an activated operating mode and start acquiring measurement data with respect to the first field of view 38 and the second field of view 42.

Alternatively or additionally, a demand signal may be received from the communication network 100 by the transmission/reception unit 32 and forwarded to the processing unit 30. The processing unit 30 then performs a wake-up of the first sensor 36 and the second sensor 40 triggered by the demand signal. Activation of the respective sensors may therefore occur independently of an object entering the third field of view 45.

The processing unit 30 may in some embodiments be configured to generate a sleep-mode signal for the first sensor 36 and the second sensor 40, causing the sensors 36, 40 to transition into a sleep mode. The sensors 36, 40 may be in sleep mode by default, wake up based upon a wake-up signal, and be sent back into the sleep mode afterwards. The sensors 36, 40 generally may consume more electric power than the passive sensor 43. Thus, by operating the sensors 36, 40 only if scene data is required, a significant amount of energy may be saved and autarkic operation of the monitoring device 20 may be fostered.

The processing unit 30 may further be configured to generate the sleep-mode signal depending upon a time period of activation of at least one of the first sensor 36 and the second sensor 40. For instance, the first sensor 36 and the second sensor 40 can be sent to sleep mode after having been operational for longer than a threshold time period. The processing unit 30 may additionally or alternatively be configured to generate the sleep-mode signal depending upon a time-period of not detecting an object by the passive sensor 43. Thus, if detection signals of the passive sensor 43 indicate that the object which caused activation of the sensors 36, 40 is no longer present and/or no longer moving, it may be decided that spatial data is no longer required since the observed scene is currently not changing. The sensors 36, 40 may then be sent to sleep mode. A sleep mode may further be initiated based upon an availability of operational power. For instance, if the energy storage unit 26 contains less than a threshold level of available energy, the sensing unit 34 may operate in an energy saving mode in which spatial data is acquired only for shorted time periods and/or only intermittently. It is also possible according to the disclosure that the sensors 36, 40 are sent to sleep mode upon reception of a sleep demand signal from the communication network 100.

The processing unit 30 may be configured for generating a primary wake-up signal for the passive sensor 43, the primary wake-up signal causing a wake-up operation of the passive sensor 43. The processing unit 30 may be configured to generate the primary wake-up signal responsive to determining that a luminosity indicated by the luminosity information of the luminosity data acquired by the luminosity sensor 41 exceeded a predefined threshold for a predefined time. This may provide a sequence of wake-up signals. First, the primary wake-up signal may cause the wake-up operation of the passive sensor 43, and next, the wake-up signal may cause the wake-up of the first sensor 36 and the second sensor 40. For instance, the luminosity may indicate daylight. It may be assumed that during the day, persons enter the patient zone more frequently. Thus, upon the luminosity indicating daylight, the passive sensor 43 might be trigger to acquire sensor data with a higher sampling rate. Upon detection, using the higher sampling rate, of a person entering the third field of view 45, the first sensor 36 and the second sensor 40 may be instructed to acquire sensor data with a higher sampling rate. Such a cascade of activations may further reduce energy consumption.

Instead of an activation of the sensors responsive to the wake-up signal, the (e.g., primary) wake-up signal may instruct the respective sensor(s) to acquire the sensor data more frequently. That is, the wake-up signal may configure the first sensor 36 and the second sensor 40 with a higher sensor sampling rate. The primary wake-up signal may configure the passive sensor 43 with a higher sensor sampling rate. Similarly, the sleep-mode signal may configure the first sensor 36 and the second sensor 40 with a lower sensor sampling rate. In other words, the sensors 36, 40 may acquire the respective sensor data with a lower sampling frequency when in the sleep mode, and with a higher sampling frequency when in the activated operating mode.

Figure 2:
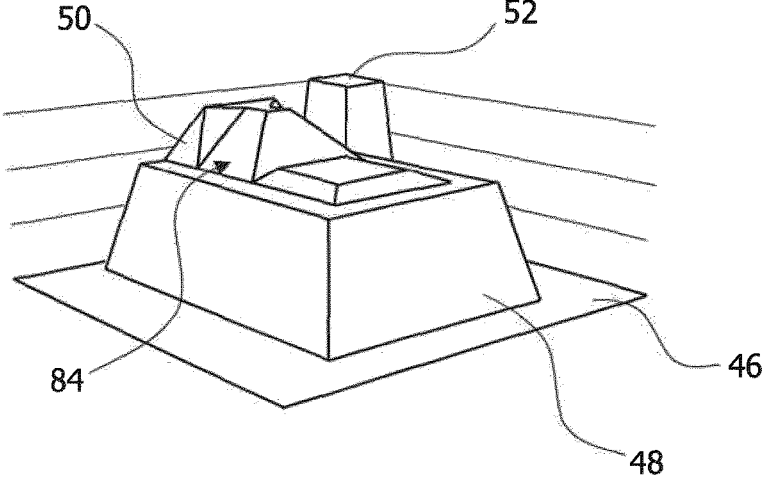
FIG. 2 shows a schematic illustration of a first set of spatial data.
Figure 3:
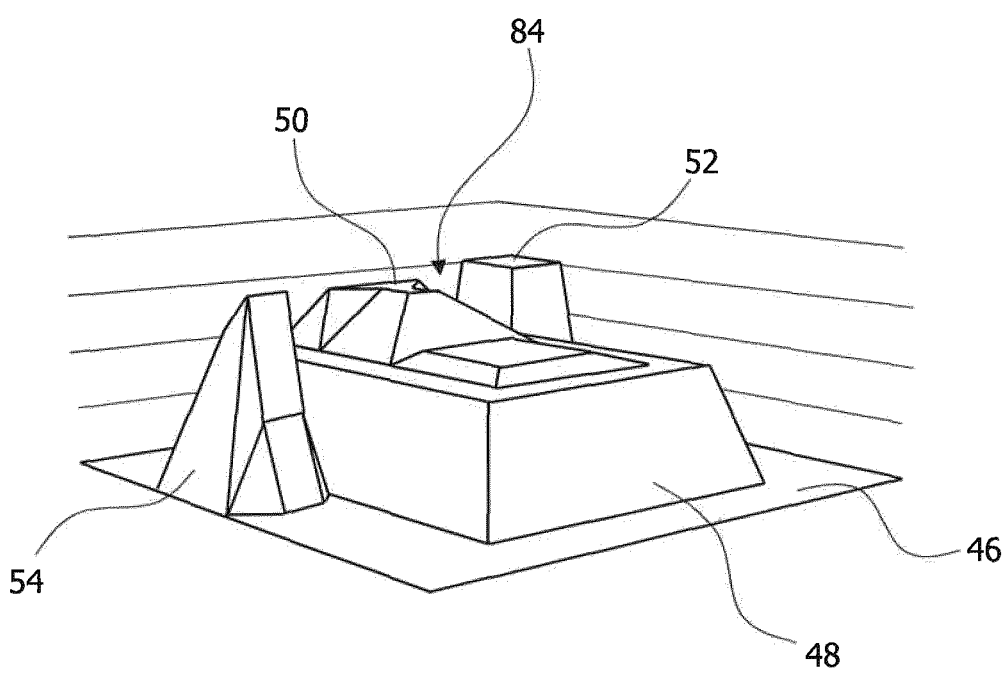
FIG. 3 shows a schematic illustration of a second set of spatial data.
Figure 4:
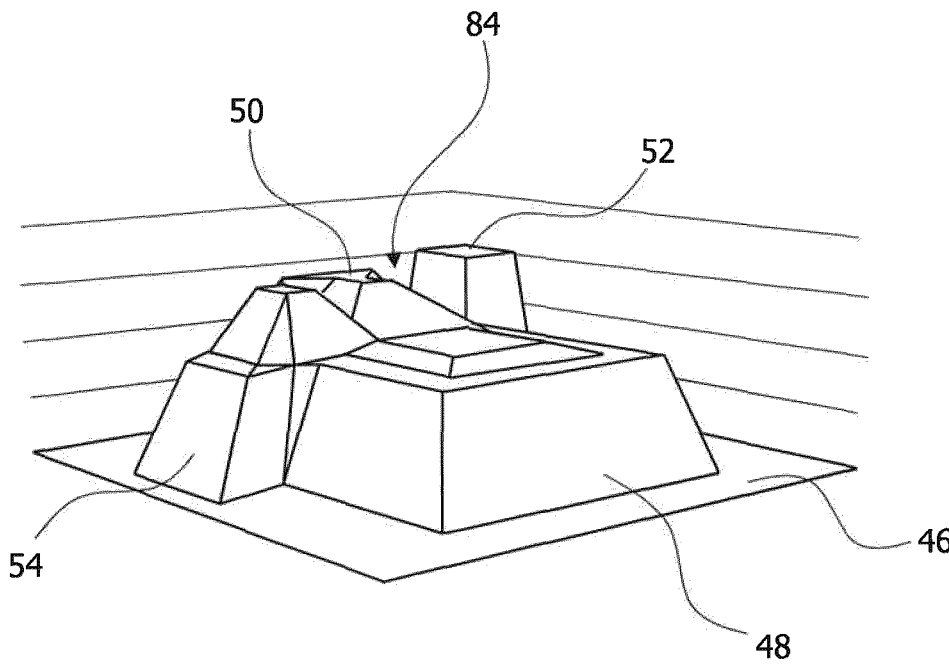
FIG. 4 shows a schematic illustration of a third set of spatial data.

Exemplary representations of spatial data obtained by the first sensing unit 34 are shown in FIGS. 2 to 4.

FIG. 2 shows spatial data corresponding to the scene shown in FIG. 1. The spatial data is that obtained by the first sensor 36 having the first field of view 38. The spatial data contains a height profile over a 2-dimensional grid. At a height level of zero, a floor data cluster 46 can be seen. In the center, a patient bed data cluster 48 is visible. Note that in the present case, owing to using a time-of-flight sensor for acquiring the spatial data, the frame structure of the patient bed 14 cannot be determined from the spatial data. Instead, the patient bed data cluster 48 corresponds to an envelope surface resulting from a projection of a top surface of the patient bed 14.

In case the first sensor 36 is tilted relative to the floor 10, the spatial data may indicate a tilted surface of the patient bed 14 and of the floor 10. One may say that the spatial data in this case is spatially distorted. To determine the spatial data as shown in FIG. 2 based on such spatially distorted data, an orientation sensor 49 (e.g., comprised in the monitoring device 20) might be used. That is, orientation data representing an orientation of the monitoring device 20 may be acquired by the orientation sensor 49. The processing unit 30 may be configured to obtain height information indicating a distance, in particular a minimal distance, between the monitoring device 20 and the floor 10, determine, on the basis of the orientation data and the height information, pose data indicative of a position and orientation of the monitoring device 20 relative to the floor 10. Furthermore, the processing unit 30 may determine use the spatial data and the pose data to determine an estimated height level of one or more surfaces of an object present within the first field of view 38, the estimated height level being determined relative to the floor 10.

The spatial data in FIG. 1 further contains a patient data cluster 50 due to the patient 16 occupying the patient bed 14. The patient bed data cluster 48 and the patient data cluster 50 merge owing to the fact that the patient 16 is lying on a bed surface of the patient bed 14.

Furthermore, the spatial data in FIG. 1 contains a clinical device data cluster 52 which is separate from the merged patient and patient bed data clusters 48, 50.

FIG. 3 shows spatial data obtained in a scene, in which the clinical personnel 44 has entered the first field of view 38 and stands next to the patient bed 14, for instance while talking to the patient 16. In addition to the above discussed data cluster, the spatial data now contains a clinical personnel data cluster 54.

FIG. 4 shows spatial data obtained in yet another scene, in which the clinical personnel 44 bends over the patient 16, for instance in order to perform treatment or examine the patient 16. In this case, the clinical personnel data cluster 54 merges with the patient bed data cluster 48 and the patient data cluster 50.

According to the disclosure, the monitoring device 20 is capable of sending to the communication network not merely spatial data of this kind, but scene data generated based upon the spatial data.

The processing unit 30 is configured to receive spatial data acquired by the sensing unit 34 and thermal data acquired by the sensing unit 35, and process at least the spatial data and the thermal data in order to generate the scene data. That is, instead of relying solely on spatially resolved depth information acquired by the first sensor 36, the processing unit 30 further considers spatially resolved thermal information acquired by the second sensor 40 to determine the scene data. This may for example enable a more reliable object classification as discussed below.

The scene data represents information with respect to a scene in a volume comprised in at least one of the first field of view 38 and the second field of view 42. The first field of view 38 at least partially overlaps the second field of view 42. The first field of view 38 overlaps the second field of view at least or only in the volume.

In case the volume is smaller than one of the first field of view 38 and the second field of view 42, the scene data may be determined only based on portions of the spatial data and the thermal data that relate to the volume where the first field of view 38 and the second field of view 42 overlap. The processing unit 30 may be configured to determine the volume where the first field 38 of view overlaps the second field of view 42, select at least one of (i) from the spatial data, a portion of the spatial data representing spatially resolved depth information with respect to the volume, and (ii) from the thermal data, a portion of the thermal data representing spatially resolved temperature information with respect to the volume, and determine the scene data based on the at least one selected portion. The monitoring device 20 may comprise at least one mask 51 arranged such that it defines at least one of the first field of view 38 and the second field of view 42. The processing unit 30 may be configured to determine the volume based on geometrical information describing an outline defined by the at least one mask 51.

The scene data includes information on at least one of presence, class and properties of one or more objects within the volume. The scene data generally represents information that relates to the presence of different objects. The scene data may represent information that relates to at least one of presence of at least one patient bed, presence of at least one occupied patient bed, presence of at least one clinical device, presence of at least one patient, and presence of at least one person, in particular clinical personnel, in the volume. The represented information may be directly contained in the scene data, whereas the data clusters discussed above inherently may not contain any information regarding their origin. Said information may be derived based upon the spatial data, the thermal data and additional knowledge.

The processing unit 30 may use various analysis approaches for generating the scene date. In a first step, a floor level may be obtained as discussed above. Furthermore, presence of a patient bed 14 may be determined based upon a comparison of the spatial data with a reference data set. A height level of a bed surface of the patient bed 14 may be obtained analogously to the floor level, for instance by finding a flat portion of a certain minimal size which can be attributed to a bed surface. A height of the patient bed 14 may thus be determined even with the patient 16 occupying it.

In a similar manner, presence of the clinical personnel 44 and/or the clinical device 18 may be determined from the spatial data.

The processing unit 30 generates the scene data further based on the thermal data acquired by the second sensor 40. To this end, the processing unit 30 may perform an object recognition on the spatial data and a parallel or subsequent object recognition or pattern recognition on the thermal data. Thermal properties of objects detected in the spatial data may be used to classify the detected objects.

The processing unit 30 may be configured to generate the scene data by (i) analyzing the spatial data to detect an object present in the volume, and by (ii) comparing, based on the thermal data, a temperature of one or more surface areas of the detected object with at least one predefined thermal property associated with at least one object class to classify the detected object. The object may be classified as being one of a person, a patient bed, a patient bed of a certain type, an occupied patient bed, a medical device, or a medical device of a certain type. Other object classes are also possible.

In some embodiments, the processing unit 30 may be configured to generate the scene data based in addition upon an analysis of at least one of spatial data obtained at different times and thermal data acquired at different times. The scene data may thus comprise information regarding when an object has entered or left the scene. Furthermore, the scene date may comprise a trajectory of a tracked object. The processing unit 30 may be configured to generate the scene data by (i) analyzing the spatial data to detect an object present in the volume, and by (ii) comparing, based on the thermal data acquired at different times, a temporal temperature behavior of one or more surface areas of the detected object with at least one predefined thermal property associated with at least one object class to classify the detected object.

The at least one predefined thermal property may be specific for objects of the at least one object class, in particular specific for certain regions of the objects of the at least one object class. The at least one predefined thermal property may be associated with a predefined region of objects of the at least one object class, wherein the one or more surface areas of the detected object are comprised in an object region of the detected object, the object region corresponding to the predefined region.

The scene data may further comprise information regarding at least one of a temporal and a spatial relationship between different objects present or detected in the volume. This may in particular be determined based upon tracking the objects over time. Consider for instance the spatial data shown in FIG. 3 and FIG. 4. From the spatial data shown in FIG. 3, scene data relating to the clinical personnel 44 may be derived since the respective clinical personnel data cluster 54 is separate from the other data clusters 46, 48, 50, 52. Tracking the clinical personnel data cluster 54 over time may allow determining that the merged data cluster shown in FIG. 4 contains three different data clusters 48, 50, 54.

In a similar manner, at least two different objects as well as their temporal and/or spatial relationship may be determined and corresponding scene data may be generated. One of the at least two different objects may be an occupied patient bed and another one of the at least two different objects may be a person, wherein the scene data represents information that relates to the person bending over the occupied patient bed.

It may be assumed that a surface temperature of a person lies between 20° C. and 45° C., whereas a room temperature may be assumed to lie between 10° C. and 30° C. A surface of a medical device may be assumed to exhibit a temperature between –20° C. and +80° C. A floor surrounding a patient bed may be assumed to have a surface temperature between 10° and 30° C. A temperature of the floor may be used as a reference value. The temperature of the floor may be determined by averaging temperatures of areas assumed to belong to the floor while disregarding temperatures of areas assumed not to belong to the floor (e.g., belonging to one or more other detected objects). The reference value may be used to determine the thermal property. The temperature of the one or more surface areas may be a relative temperature between the reference value and a measured temperature of the one or more surface areas.

The second sensor may have a temperature measurement range between –20° C. and 80° C. or between –20° C. and one or several hundred degrees Celsius. The one or more surface areas of a detected patient bed may be a head portion of the bed, a middle portion of the bed or a foot portion of the bed. The one or more surface areas of a detected medical device may comprise a surface of a heat sink or a heat emitter of a medical device. The processing unit 30 may be configured to distinguish between one or more adjacent surfaces having a similar current thermal property by comparing thermal properties of the one or more adjacent surfaces over time. This may allow distinguishing between different spatially overlapping or spatially adjacent objects.

The processing unit 30 may use estimated volumes, estimated footprints and/or estimated surfaces of the different objects. For instance, the processing unit 30 may compare a volume derived from the data cluster caused by the merged patient data cluster 50 and patient bed data cluster 40 to the volume derived from the data cluster caused by the merged patient data cluster 50, patient bed data cluster 40 and clinical personnel data cluster 54. In addition, the processing unit 30 may determine a volume based upon the clinical personnel data cluster 54 from the spatial data of FIG. 3, where the clinical personnel data cluster 54 is relatively isolated. Comparing all these volumes may allow the conclusion that the clinical personnel 44 is bending of the patient 16. The scene data may therefore comprise, based upon the spatial data shown in FIGS. 2 to 4 and the corresponding times, for instance, the information that the clinical personnel 44 has entered the first field of view 38, has interacted with the patient 16 while standing next to the patient bed 14, and has finally bent over the patient 16 for performing treatment. The scene data may be generated based on the estimated height level described herein.

The passive sensor 43 may be configured to generate a sensing signal responsive to an object entering or exiting the third field of view 45. The processing unit 30 may be configured to receive the sensing signal from the third sensing unit 37 and generate the scene data further based on the sensing signal. For instance, the processing unit 30 may determine that an object has moved into the third field of view based on the sensing signal, and track movement of this object within the volume where the first field of view 38 overlaps the second field of view 42. It is noted that portions where the first field of view 38 does not overlap the second field of view 42 may also be considered for determining the scene data. For example, the processing unit 30 may determine that the object, after having entered the third field of view 45, has entered the second field of view 42, based on the thermal data. The processing unit 30 may be configured to determine that the same object then enters the first field of view 38 based on the spatial data and, optionally, further based on the thermal data related to the volume.

In the embodiment shown in FIG. 1, to which reference is made again in the following, the monitoring device 20 is further configured to receive signals from different low-energy beacons. Specifically, there may be a clinical personnel beacon 56, a patient beacon 58, a patient bed beacon 59 and a clinical device beacon 62 to name only some possibilities. The beacons 56, 58, 59, 62 may contain an ID and/or other information regarding properties of the carrying object.

The transmission/reception unit may be configured to determine an ID of at least one or all of these beacons 56, 58, 59, 62. Furthermore, the transmission/reception unit may be configured to determine a distance to at least one or all of these beacons 56, 58, 59, 62. The distance may for instance be determined using RSSI (Received Signal Strength Indication).

Alternatively or additionally, the processing unit 30 may be configured to determine identities and/or distances of objects present in the first field of view 38 directly from the spatial data. The respective object may carry an optically detectable label. Information corresponding to this label may then be derivable based upon a suitable data analysis of the spatial data. For instance, the patient bed 14 may comprise a label with a textured surface, similar to Braille, which textured surface may function as information carrier. In embodiments where a camera is used as active sensor color information and/or other image information may be derived from the spatial data. Alternatively or additionally, the processing unit 30 may be configured to determine the identities and/or distances of the objects present in the first field of view 38 directly from or additionally based on the thermal data. The object classes may comprise a class for each identity.

The identity may further be obtained from a comparison with stored data. For instance, if a patient identity is available from a database together with the information that said patient 14 will arrive in the patient room where the monitoring device 20 is mounted, the monitoring device 20 may store a patient profile and use this patient profile to recognize the specific patient 14 again. The same may be the case for clinical personnel 44.

It is further conceivable according to the disclosure that data obtained from at least one beacon is combined with at least one of spatial data and thermal data for determining an identity and/or a distance of an object. Beacon data may further be used to generally determine presence of an object. For instance, if beacon data obtained by the transmission/reception unit 32 indicates that three different persons of clinical personnel are present, the processing unit 30 may take this information into account when analyzing the spatial data and the thermal data. Furthermore, if a spatial data cluster is observed which apparently corresponds to a person but no associated beacon is detected, it may be concluded that the person is not clinical personnel. Generally speaking, a combination of beacon data and at least one of spatial data and thermal data may be used to obtain more precise spatial data. This may comprise plausibility checks as well as complementation of analysis results.

Thus, the processing unit 30 is generally configured to generate the scene date such that it represents information regarding at least one of the following: presence of an empty patient bed 14; presence of an occupied patient bed 14; presence of an empty patient bed 14 of a certain type; presence of an occupied patient bed 14 of a certain type; presence of a clinical device 18; presence of a clinical device 18 of a certain type; presence of at least one person; presence and identity of at least one person; presence of clinical personnel 44; presence and identity of clinical personnel; interaction between clinical personnel and a patient; interaction between clinical personnel and a patient zone; presence of clinical personnel before an interaction with a patient; presence of clinical personnel after interaction with a patient; presence of clinical personnel after interaction with a patient zone; absence of clinical personnel after interaction with the patient; absence of clinical personnel after interaction with the patient zone; presence of clinical personnel before an aseptic activity; presence of clinical personnel after an aseptic activity; presence of a patient in a certain acute condition; amount of movement of a patient during a certain time period; and presence of a patient who has fallen out of a bed.

Figure 5:
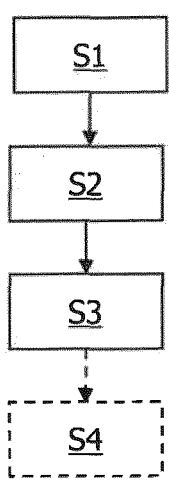
FIG. 5 shows a flowchart illustrating a clinical method.

FIG. 5 shows a flowchart of an exemplary clinical method according to the disclosure. The clinical method comprises using the monitoring device 20. The clinical method comprises a step S1 of obtaining the spatial data (e.g., representing 3-dimensional information with respect to the first field of view 38 of the sensing unit 34). The clinical method further comprises a step S2 of obtaining the thermal data (e.g., representing spatially resolved temperature information of surfaces within the second field of view 42), and a step S3 of processing the spatial data and the thermal data to generate the scene data (e.g., representing information with respect to a scene in the volume, wherein, optionally, the scene data represents information that relates to at least one of presence of at least one patient bed 14, occupation of at least one patient bed 14, presence of at least one clinical device 18, presence of at least one patient 16, and presence of at least one person, in particular clinical personnel 44, in the first field of view 38 of the sensing unit 34). The clinical method may further comprise a step S4 of transmitting the scene data over a communication network 100. Steps S1 to S4 may be performed by the processing unit 30.

In some embodiments, the clinical method may further comprise a step of receiving the scene data over the communication network 100. As will be described below, the scene data may be received by a server, any suitable monitoring unit, a terminal etc.

Reference is again made to FIG. 1. Within an area of concern 70 such as the patient room, a hygiene dispenser 59 may be present according to some embodiments. The hygiene dispenser 59 allows a person using it sanitizing hands. As mentioned above, there are different situations conceivable in which hand sanitation is indicated, such as prior to interacting with the patient 14 or after interacting with the patient 14 and leaving the patient room or attending to another patient.

The hygiene dispenser 59 is part of a monitoring system 60, which will be described in more detail below. The monitoring system 60 comprises a treatment detection unit 63 configured to detect a disinfection treatment performed with the hygiene dispenser 59. The treatment detection unit 63 comprises for instance a sensor 64 arranged on and/or integrated in the hygiene dispenser 59. The sensor 64 is configured to acquire at least one parameter indicative of usage of the dispenser. The treatment detection unit 63 may contain stored information regarding an ID and/or location of the hygiene dispenser 59.

In some embodiments, the treatment detection unit 63 may be configured to determine an amount of disinfectant used.

The monitoring system 60 further comprises a portable device 64. The portable device 64 is configured to be carried and/or worn by a person, in particular by the clinical personnel 44. The portable device 64 carries an ID, which may be associated with a type of clinical personnel 44 or with an individual person. In some embodiments, the clinical personnel beacon 54 may be included in the portable device 64.

The disclosed system may function anonymously such that only a personnel type is associated with a unique ID of a portable device 64. In this case, the portable device 64 may indicate movement and/or behavior of the person wearing it together with the information to which type of clinical personnel 44 said person belongs. However, it may not be apparent therefrom which individual person is monitored.

The treatment detection unit 63 is configured to detect presence of the portable device 64. The treatment detection unit 63 determines an estimated distance between the portable device 64 and the hygiene dispenser 59. Based thereupon, it can be estimated whether or not usage of the hygiene dispenser 59 is associated with the portable device 64 and thus with the person using it. For instance, in case the distance is determined to be smaller than a certain threshold while the hygiene dispenser 59 is being used, it is determined that the person wearing the portable device has sanitized hands. In other embodiments, the portable device 64 may additionally or alternatively detect presence of and/or a distance to the hygiene dispenser 59.

The portable device 64 and/or the treatment detection unit 63 may be configured to send data to and/or receive data from the communication network 100, for instance by means of a suitable transmission/detection unit.

The treatment detection unit 63 is generally configured to identify the portable device 64. Furthermore, the treatment detection unit 63 is configured to identify the portable device

64, and generate treatment data representing information regarding the detected treatment and the identified portable device 64.

The monitoring system 60 comprises a monitoring unit 66. The monitoring unit 66 comprises at least one processor. The monitoring unit 66 further comprises a data storage and a transmission/reception unit configured to send data to and receive data from the communication network 100. The monitoring unit 66 may be part of a device arranged within the area of concern. The monitoring unit 66 may alternatively be implemented on any computing device connected to the communication network. The monitoring unit 66 may in particular be arranged outside of the patient room. This will be described below in further detail with reference to FIG. 6.

The monitoring unit 66 is configured to receive the treatment data from the treatment detection unit 63. The monitoring unit 66 further receives and/or determines a time of the disinfection treatment. Accordingly, the information is available that a disinfection associated with the portable device 64 and hence with the clinical personnel 44 carrying it has been performed at a certain time at a certain hygiene dispenser 59.

Furthermore, the monitoring unit 66 is generally configured to receive the scene data from the monitoring device 20 and process the scene data. The monitoring unit 66 is further configured to determine a hygiene status based upon the treatment data and the scene data, and assign the hygiene status to the portable device 64.

The hygiene status may be determined based upon the amount of disinfectant used. The WHO recommends using at least 3 ml of disinfectant for proper hand sanitation. In some embodiments, the monitoring unit 66 may compare the determined amount of disinfectant used to a threshold value and set the hygiene status to "acceptable" only in case this threshold is reached or exceeded. Hand sanitation using an insufficient amount of disinfectant will then not be considered.

In some embodiments, the location of the hygiene dispenser 59 may be taken into account. A digitized floor plan of at least a portion of the clinical or medical facility may be used. The location of the hygiene dispenser 59 may be stored with respect to a digitized floor plan. Priorities and/or importance values may be assigned to a hygiene dispenser 59 or to different hygiene dispensers depending upon it/their location. Furthermore, the monitoring unit 66 may be configured to determine an average and/or accumulated usage, and/or an average and/or accumulated amount of disinfectant used as a function of the location of the hygiene dispenser 59. Any of these values and/or information may be taken into account when determining the hygiene status.

In the present case, the following may exemplarily occur, illustrating the functionality of the monitoring system. The clinical personnel 44 enters the room and sanitizes hands using the hygiene dispenser 59. Respective treatment data is generated by the treatment detection unit 63 and received by the monitoring unit 66. The clinical personnel 44 then enters the fields of view 38, 42 and corresponding scene data is generated by the monitoring device 20 and received by the monitoring unit 66. The monitoring unit 66 determines that the situation represented by the scene data is prior to interaction with a patient. The monitoring unit 66 determines an elapsed time since the hand sanitation has taken place and compares it to a threshold value. Furthermore, the monitoring unit 66 determines, based upon the scene data, that no hygiene-relevant events have occurred in the meantime. The monitoring unit 66 then assigns the hygiene status "acceptable" to the portable device 64.

Determining that a hygiene-relevant event has occurred can be based on a time during which the personnel 44 is present within one or more of the fields of view 38, 42, 45. Different trigger times may be used for the different fields of view 38, 42, 45 and for different regions within the fields of view 38, 42, 45. For example, in case the personnel 44 is present in a first region at a side of a head portion of the patient bed 14 for longer than 30 seconds, it may be assumed that a contact between the personnel 44 and the patient 16 has taken place. That is, occurrence of a hygiene-related event may be determined. The same may be the case for the personnel 44 being present in a second region at a side of a foot portion of the patient bed 14 for longer than 90 seconds, or for the personnel 44 being present in a third region at the end of the patient bed 14 at a foot portion thereof for longer than 180 seconds.

At a later point in time, the clinical personnel 44 may be about to perform an aseptic activity. The monitoring unit 66 determines the situation to be before an aseptic activity. An additional hand sanitation is required. Since the clinical personnel 44 has not yet used the hygiene dispenser 59 again, the monitoring unit 66 sets the hygiene status of the portable device 64 to unacceptable.

In the present embodiment, the portable device 64 is configured to receive the hygiene status from the monitoring unit 66 and to generate at least one perceptible output indicative of the hygiene status. The perceptible output comprises at least one of an audio signal, a haptic signal, a visual signal, a vibration signal, an image, an animation and a light color. For instance, if the portable device 64 generated a vibration signal, the clinical personnel 44 is reminded that an additional hand sanitation is due and is motivated to use the hygiene dispense 58 before attending to the aseptic activity.

Additionally or alternatively, the monitoring system 60 may comprise at least one output device 68 arranged in the area of concern 70. The output device 68 is configured to receive the hygiene status from the monitoring unit and to generate at least one perceptible output indicative of the hygiene status. In the present embodiment, the output device 68 is a display device arranged in the patient room. Depending on the current hygiene status of the portable device 64, a positive indication such as a smiling face, a green icon, a short text message or the like, or a negative indication such as a frowning or sad face, a red icon, a short text message or the like is displayed.

The monitoring system 60 of this embodiment functions as hygiene compliance monitoring system. The monitoring system 60 allows for automatization of compliance observation and provides faster feedback to the clinical personnel 44.

The monitoring unit 66 may further generate and store a hygiene log from which past hygiene statuses are apparent. It can then for instance be determined which type of clinical personnel 44 complies with hygiene provisions in which situations. The monitoring unit 66 may be configured to generate graphical and/or textual analysis information such as statics.

In other embodiments, the hygiene status may be directly assigned to objects identified based on the scene data as described above. The monitoring system 60 may then in principle function without a portable device. In such embodiments, it is advantageous if the hygiene dispenser 59 is within the first field of view 38 such that a disinfection treatment being performed can be derived from the spatial data.

Figure 6:
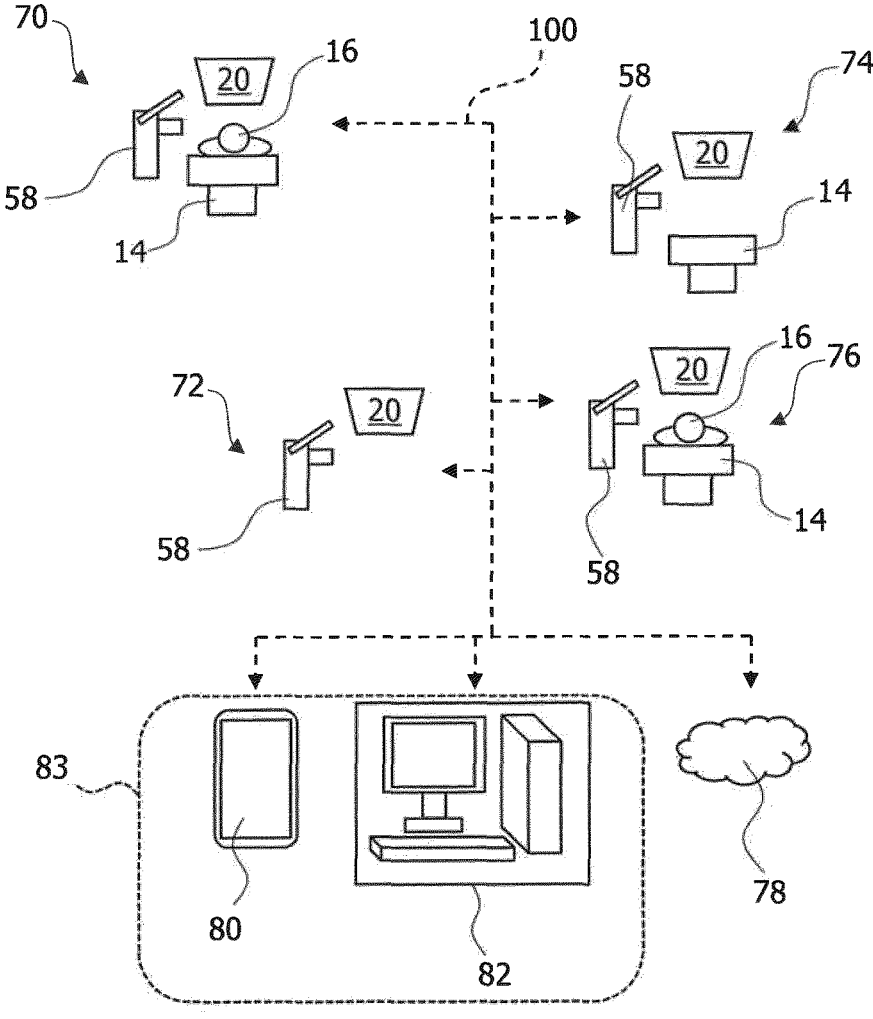
FIG. 6 shows a schematic diagram of a monitoring system comprising the monitoring device.

FIG. 6 shows a schematic diagram of the monitoring system 60. In the present case, the monitoring system 60 comprises a plurality of different monitoring devices 20 in a plurality of different areas of concern 70, 72, 74, 76. The different areas of concern 70, 72, 74, 76 are for instance different patient rooms. The monitoring devices 20 may each be arranged such that a region designated for placing a patient bed is within the respective fields of view. In the exemplary embodiment, each area of concern 70, 72, 74, 76 is further equipped with a hygiene dispenser 59. The method and functions described above may therefore generally be performed in each of the areas of concern 70, 72, 74, 76.

The monitoring system 60 further comprises a communication network. Furthermore, the monitoring system 60 comprises a server 78 and several terminals 80, 82, two of which are exemplarily shown. At least one terminal 80 is a mobile terminal in the shown embodiment. Terminals may be any type of computing devices with a user interface, such as desktop computers, mobile phone, tablet computers, smart wearables etc. The server 78 may for instance be a cloud server, a local server or a dedicated server.

The one or more terminals 80, 82 can be generally considered as output unit 83.

The monitoring unit 66 may be part of or implemented on the server 78. Additionally or alternatively, the monitoring unit 66 may be part of or implemented on any or several of the terminals 80, 82. The monitoring unit 66 may in particular be implemented as shared unit with several devices contributing processing performance and/or data storage.

Using any of the terminals 80, 82, a user may interact with the monitoring system 60. The monitoring unit 66 may be configured to generate display data for a display device of at least one terminal 80, 82. Furthermore, the monitoring unit 66 may be configured to process user input received from at least one of the terminals, for instance in order to implement interactive display functionalities. A user may thus inspect the results of different monitoring operations, view scene data, view statistics etc.

In some embodiments, in addition or as an alternative to the monitoring device 20 being configured to generate the scene data such that it represents information regarding at least one of the above-mentioned situations, presences of objects, etc., the monitoring unit 66 may be configured to modify the scene data received from the monitoring device 20 such that it represents the respective information. The scene data may in these cases comprise information processed to a less detailed degree. Scene data may then be complemented based on additional processing steps performed by the monitoring unit 66, such as adjusting the hygiene status of the portable device 64.

It is further envisaged by the disclosure that in some embodiments the monitoring device 20 itself performs the functions of the monitoring unit 66.

The monitoring system 60 of the present embodiment is further configured to provide a bed occupation monitoring. For this purpose, the monitoring unit 66 is configured to receive scene data from each of the plurality of monitoring devices 20. Based on this scene data, the monitoring unit 66 generates bed occupation data representing information regarding presence and occupation state of different patient beds 14 present in the different areas of concern.

In the exemplarily shown case, patient beds 14 are present in the three areas of concern denoted 70, 74 and 76. No patient bed is present in the area of concern denoted 72. The patient beds 14 in the areas of concern denoted 70 and 76 are occupied. The patient bed 14 in the area of concern denoted 74 is unoccupied. The respective scene data is generated by the respective monitoring device 20. As mentioned above, the scene data can be more precise if a patient ID and/or a patient bed ID 14 and/or a patient bed type are determined, for instance using one or more of the beacons 56, 58, 59, 62 described above. In addition, the respective scene data for the different areas of concern 70, 72, 74, 76 and/or the different patient beds 14 may comprise information regarding clinical devices 18 present.

Using this information, an overview plan can be generated by the monitoring device 66 and output by the output unit 63 to a user containing information regarding a current bed occupation. As discussed before, this output may be interactive. For instance, the user may request statistics regarding availability of beds of a certain type, location of beds within the clinical facility, track a certain bed, track a certain patient etc. By means of such an automated patient bed occupation monitoring, patient capacities may be easily, reliably and precisely determined, in particular without human error. The related data and/or information may be sent to other internal or external systems via a suitable interface, for instance to a local, central, national or international hospital bed information system.

The monitoring system 60 of the present embodiment may also serve as patient monitoring system. The monitoring unit 60 may be configured to generate, on the basis of the scene data, patient monitoring data. The patient monitoring data can be, in particular interactively, output to a user via the output unit 83.

Patient monitoring may be performed by evaluating a temporal evolution of height information of a region associated with a patient with respect to a region associated with a bed surface of a patient bed. The monitoring unit 66 may be configured to determine an amount of patient movement over time based upon this temporal evolution. Scene data can therefore be used to determine how much and in which way a patient moves, for instance if the patient 14 turns regularly, leaves the patient bed 16, has fallen out of the patient bed 14 etc.

As indicated in FIGS. 2, 3 and 4, a suitable region is for instance the chest region of the patient. A chest region data cluster 84 of the spatial data may change periodically while the patient 14 breathes in and out. If a respective time period is derived from movement of the chest region data cluster 84, a breathing rate can be determined.

Furthermore, a risk for pressure sores can be determined based upon temporal monitoring of patient movement. This risk can for instance be assessed by the monitoring unit 66 based on comparison of an amount of patient movement with a threshold.

In other embodiments, the processing unit 30 of the monitoring device 20 may be configured to analyze patient movements in order to generate patient monitoring data. The patient monitoring data can then be included in the scene data or sent separately to the monitoring unit 66.

Patient monitoring data may generally be sent to other patient monitoring and/or administration systems. For instance, the monitoring data and/or data derived therefrom due to further processing may be included in a digital patient file. This may enable an automated documentation and reduce the amount of manual work.

With reference to FIG. 6, patient monitoring can be performed for several patients simultaneously. In the shown exemplary embodiment, the monitoring unit 66 is configured to generate alerts based on monitored patient data, for instance in case a breathing rate of a certain patient falls below a certain threshold or in case a risk for pressure sores exceeds a certain threshold.

In case of the described patient monitoring and/or in case of the described patient bed occupation monitoring, a wake-up of the respective active sensor 36 of the respective monitoring device 20 in a certain area of concern 70, 72, 74, 76 and/or in a certain patient room may be triggered by sending a demand via the communication network. For instance, monitoring may occur in regular intervals, inter-mittently and/or upon a user request. Monitoring may be performed only for selected areas of concern 70, 72, 74, 76 or for all areas of concern 70, 72, 74, 76. It should be noted that data acquisition by the first sensor 36 and the second sensor 40 in such monitoring scenarios may be performed also in case the passive sensor 43 does not detect presence or movement of an object.

As noted above, the disclosure also encompasses moni-toring systems in which one or more functions of the processing unit 30 of the monitoring device 20 are imple-mented by a processing unit outside of the monitoring device 20. The monitoring device 20 may then sent spatial data via the communication network 100, and scene data may be generated alternatively or additionally by said pro-cessing unit receiving the spatial data via the communication network 100.

It is apparent from the above description of embodiments according to this disclosure that the disclosure encompasses the following clinical methods.

Figures 7, 8, 9, 10:
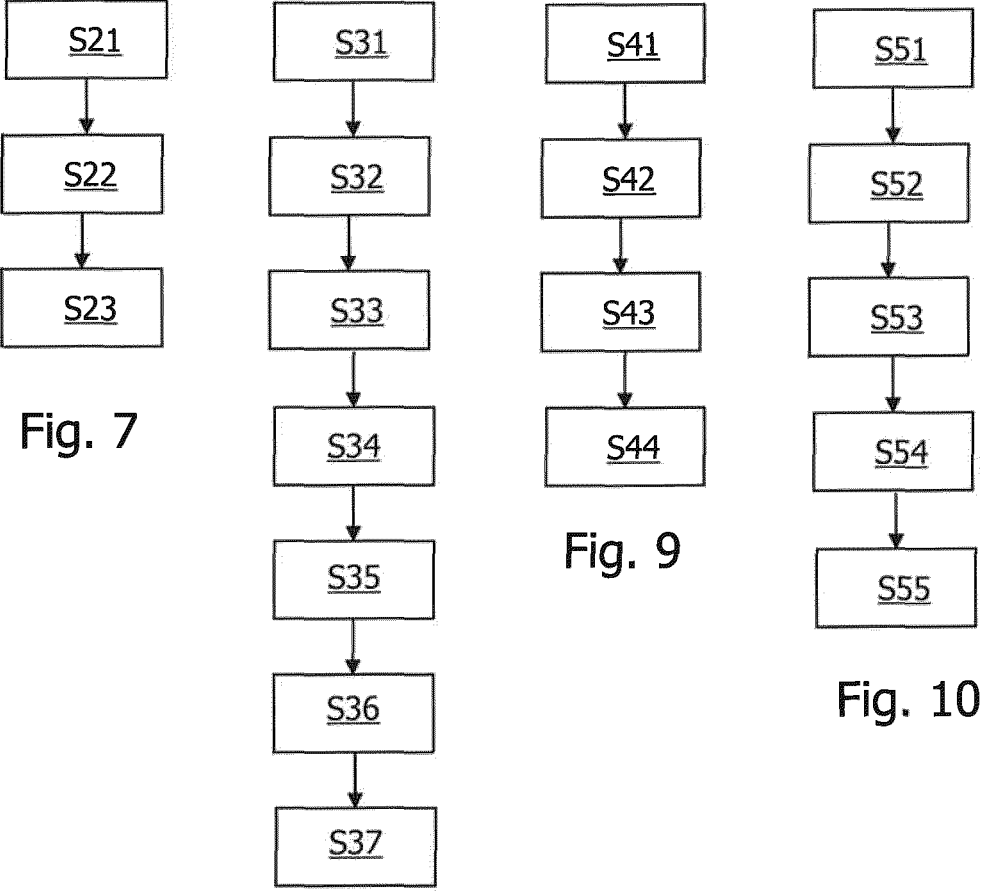
FIGS. 7 to 10 show flowcharts of other clinical methods.

As illustrated in FIG. 7, a clinical method according to the disclosure generally comprises using a monitoring system 60 according to the disclosure. The method comprises a step S21 of generating, with the monitoring device 20, scene data. The method further comprises a step S22 of receiving, with the monitoring unit 60, the scene data. In addition, the method comprises a step S23 of processing, with the moni-toring unit 60, the scene data.

As illustrated in FIG. 8, a clinical method for monitoring hygiene compliance comprises using a monitoring system 60 according to the disclosure. The method comprises a step S31 of providing clinical personnel 44 with the portable device 64; a step S32 of detecting, with the treatment detection unit 63, a disinfection treatment performed by the clinical personnel 44 due to identification of the portable device 64; a step S33 of generating, with the treatment detection unit 63, treatment data representing information regarding the detected treatment and the identified portable device 64; a step S34 of generating, with the monitoring device 20, scene data relating to the respective area of concern 70, 72, 74, 76; a step S35 of receiving, with the monitoring unit 66, the treatment data and the scene data; a step S36 of determining, with the monitoring unit 66, a hygiene status based upon the treatment data and the scene data; and a step S37 of assigning, with the monitoring unit 66, the hygiene status to the portable device 64.

The step S36 may comprise determining, on the basis of the scene data, that clinical personnel 44 is in at least one of the following situations: before interaction with a patient 16, before an aseptic activity, after contact to infectious mate-rial, after interaction with a patient 16, and after interaction with a patient zone; and determining, on the basis of the treatment data, whether or not clinical personnel 44 has sanitized hands before or in said situation.

As illustrated in FIG. 9, a clinical method for monitoring availability of patient beds 14 in a medical facility comprises using a monitoring system 60 according to the disclosure. The method comprises a step S41 of generating, with the plurality of monitoring devices 20, respective scene data relating to the different areas of concern 70, 72, 74, 76; a step S42 of receiving, with the monitoring unit 66, the scene data from each of the plurality of monitoring devices 20; a step S43 of generating, with the monitoring unit 66, bed occu-pation data representing information regarding presence and occupation state of different patient beds 14 present in the different areas of concern 70, 72, 74, 76; a step S44 of receiving, with the output unit 83, the bed occupation data from the monitoring unit 66; and a step S45 of outputting, with the output unit 83, the bed occupation data to a user.

As illustrated in FIG. 10, a clinical method for patient monitoring comprises uses a monitoring system 60 accord-ing to the disclosure. The method comprises a step S51 of generating, with the monitoring device 20, scene data; a step S52 of receiving, with the monitoring unit 66, the scene data; a step S53 of generating, with the monitoring unit 66, patient monitoring data on the basis of the scene data; a step S54 of receiving, with the output unit 83, the patient monitoring data; and a step S55 of outputting, with the output unit 83, the patient monitoring data.

Figure 11:
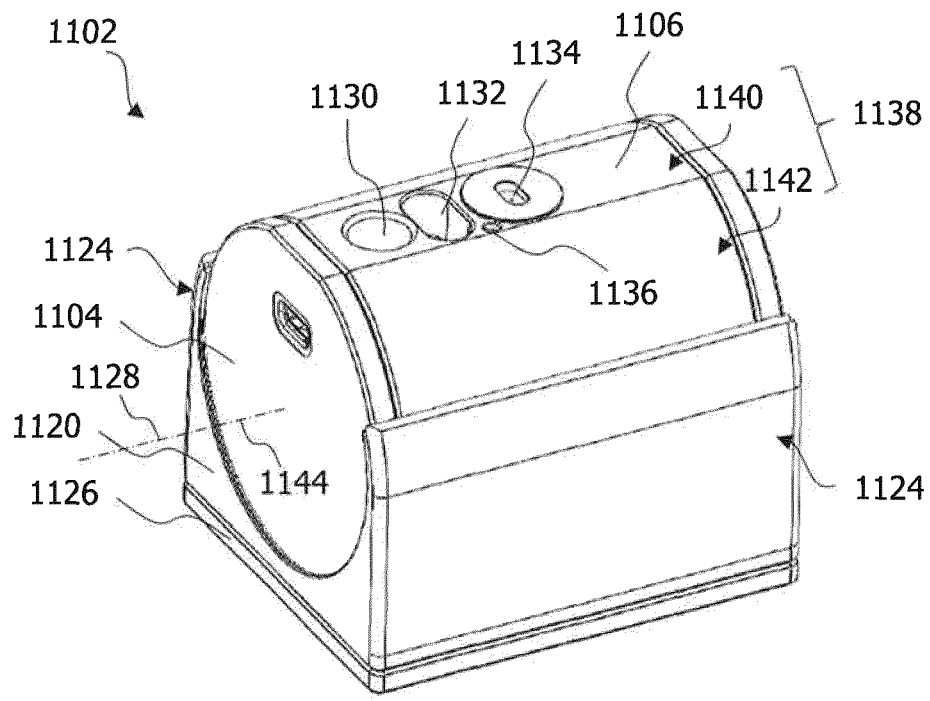
FIG. 11 shows a schematic illustration of a monitoring device.
Figure 12:
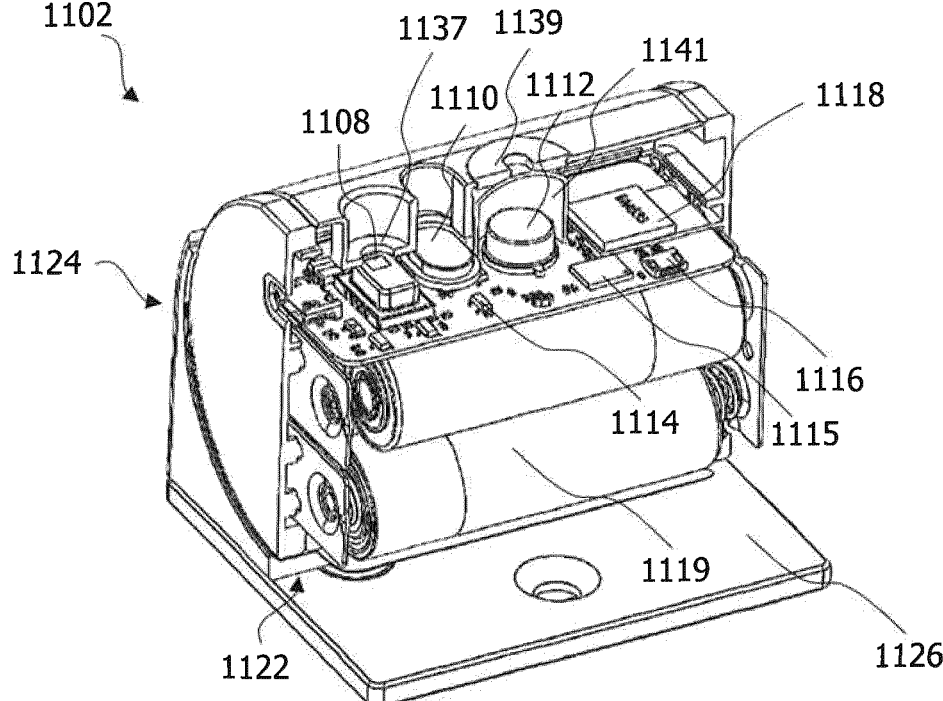
FIG. 12 shows a schematic illustration of the monitoring device of FIG. 11 with a part of the housing removed.

FIG. 11 shows an illustration of a clinical monitoring device 1102, in particular in particular a patient zone moni-toring device. The device 1102 may correspond to the device 20 described above. The device 1102 comprises a housing 1104 having a first side 1106. The housing 1104 may correspond to the housing 22. FIG. 12 shows an illustration of the device 1102 with a portion of the housing 1104 removed.

The device 1102 comprises at least one sensor 1108, 1110, 1112, 1114 arranged at the first side 1106 of the housing 1104. In the shown example, each of the at least one sensor 1108, 1110, 1112, 1114 is arranged within the housing 1104, which means it is housed by the housing 1104. The sensor 1108 may correspond to the first sensor 36 described herein (e.g., the sensor 36). The sensor 1110 may correspond to the second sensor described herein (e.g., the sensor 40). The sensor 1112 may correspond to the passive sensor described herein (e.g., the sensor 43). The sensor 1114 may correspond to the luminosity sensor described herein (e.g., the sensor 41).

A wireless data transmission unit 1116 may also be arranged within the housing 1104. The transmission unit 116 may correspond to the transmission/reception unit 32. The device 1102 may comprise a processor 1118. The processor 1118 may be electrically connected to the at least one sensor 1108, 1110, 1112, 1114 and the wireless data transmission unit 1116. The processor 1118 may be arranged within the housing 1104. The processor 1118 may correspond to the processor of the processing unit 30. The device 1102 may comprise an energy storage unit 1119 arranged within the housing 1104. The energy storage unit 1119 may correspond to the energy storage unit 26 described above.

The device 1102 further comprises a retainer 1120. The retainer 1120 may correspond to the mounting unit 24 described above. The retainer 1120 comprises a coupling portion 1122 and a holding portion 1124. The coupling portion 1122 is configured to be coupled to a stationary mounting 1126. Alternatively or additionally, the coupling portion 1122 may be configured to be fixed to a ceiling or a wall, for example using screws. The holding portion 1124 is holding the housing 1104. The holding portion 1124 is configured to hold the housing 1104 such that the housing 1104 is rotatable around a first rotation axis 1128. This may allow an adjustment of a viewing direction of the at least one sensor of the device 1102, for example in such a way that the at least one sensor is able to monitor a patient bed. In other words, the rotation of the housing 1104 within the retainer 1120 allows for adjustments to the orientation of the housing 1104 relative to the retainer 1120 and, thus, relative to a wall or ceiling at which the retainer 1120 may be arranged.

The holding portion 1124 may be configured to hold the housing 1104 such that the only possible relative movement between the housing 1104 and the holding portion 1124 is a rotation around the first rotation axis 1128. The housing 1104 may be rotatably supported by the holding portion 1124.

The housing 1104 may comprise at least one opening 1130, 1132, 1134, 1136 within the first side 1106 of the housing 1104. The at least one sensor 1108, 1110, 1112, 1114 may be arranged within the housing and adjacent to the at least one opening 1130, 1132, 1134, 1136 such that a field of view of the at least one sensor 1108, 1110, 1112, 1114 extends through the at least one opening 1130, 1132, 1134, 1136 to an exterior of the housing 1104. In the illustrated example, separate openings 1130, 1132, 1134, 1136 are provided in the first side 1106, each associated to one of the sensors 1108, 1110, 1112, 1114. The first side 1106 of the housing 1104 may face away from the coupling portion 1124. This may provide an unobstructed view for the at least one sensor. A (e.g., transparent) cover may be provided over one or more of the at least one opening 1130, 1132, 1134, 1136. This may avoid dust from entering the housing 1104.

The device 1202 may comprise one or more masks 1137, 1139. One or the one or more masks 1137, 1139 may correspond to the mask 51. Each of the masks 1137, 1139 may be arranged at one of the sensors 1108, 1110, 1112, 1114. In the shown example, the mask 1137 is provided in a viewing direction of the sensor 1108 and the mask 1139 is provided in a viewing direction of the sensor 1112. The mask 1137 may define a contour, an outline or a shape of a first field of view of the sensor 1108 (e.g., the first field of view 38). The mask 1139 may define a contour, an outline or a shape of a third field of view of the sensor 1112 (e.g., the third field of view 45). The one or more masks 1137, 1139 may be adjustable in size and/or form, for example by a user or based on a control signal (e.g., provided by the processor 1118).

The device 1202 may comprise one or more lenses 1141. Each lens 1141 may be arranged at one of the sensors 1108, 1110, 1112, 1114. In the shown example, the lens 1141 is a Fresnel lens provided in a viewing direction of the sensor. The lens 1141 may define a contour, an outline or a shape of the third field of view of the sensor 1112 (e.g., the third field of view 45).

The housing 1104 may comprise an outer housing surface 1138. The outer housing surface 1138 may comprise a cylindrical surface portion 1142 having a cylinder axis 1144. The cylinder axis 1144 may coincide with the first rotation axis 1128. The outer housing surface 1138 may comprise a flat surface portion 1140. The flat surface portion 1140 may be arranged at or correspond to the first side 1106 of the housing 1104.

Figure 13:
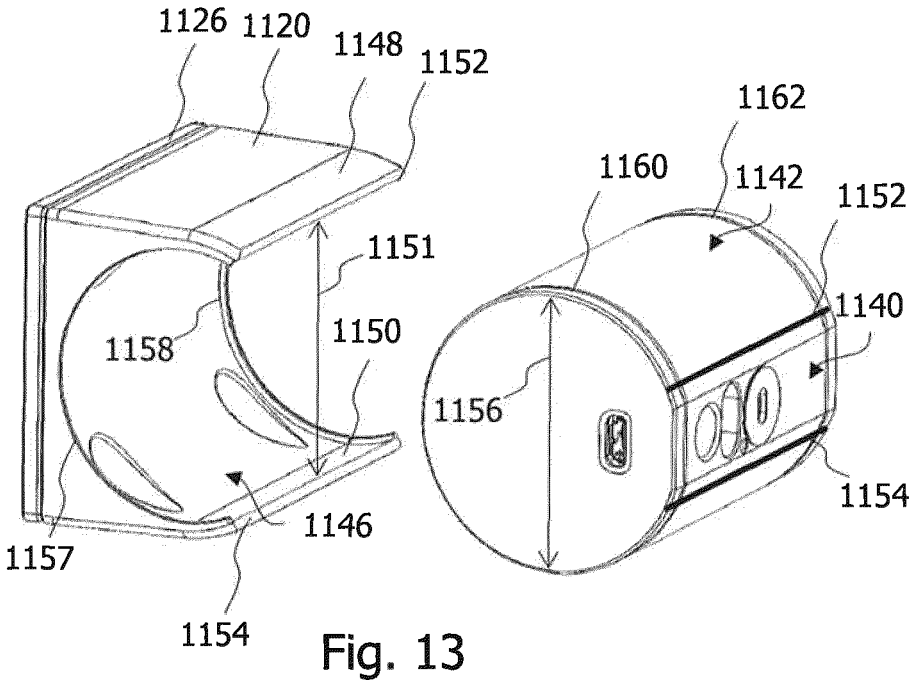
FIG. 13 shows a housing of a monitoring device separated from a retainer of the monitoring device.

FIG. 13 shows an explosion drawing in which the housing 1104 is removed from the retainer 1120. As can be seen, the holding portion 1124 may comprise a contact surface 1146 matching the cylindrical surface portion 1142. The contact surface 1146 may be in contact with (e.g., a portion of) the cylindrical surface portion 1142 when the housing 1104 is held by the retainer 1120. This may enable a secure holding of the housing 1104.

The holding portion 1124 may comprise one or more retaining members 1148, 1150 extending circumferentially relative to the cylindrical surface portion 1142 (e.g., when the housing 1104 is held by the retainer 1120). The holding portion 1124 may comprise (e.g., exactly) two retaining members 1148, 1150 extending in opposite directions. A distance 1151 between a distal end 1152, 1154 of each of the retaining members 1148, 1150 may be smaller than a diameter 1156 of the cylindrical surface portion 1142. Each of the one or more retaining members 1148, 1150 may extend along an axis parallel to at least one of the first rotation axis 1128 and the cylinder axis 1144. The retaining members 1148, 1150 may be configured to block of from the housing 1104 from the retainer 1120. This may prevent the housing 1104 from (e.g., unpredictably) falling out of the retainer 1120 (e.g., onto a patient bed) when the device 1102 is attached to a wall or a ceiling.

The holding portion 1124 may be configured to hold the housing 1104 such that the housing 1104 is rotatable around the first rotation axis 1128 within a predefined range of rotation angles. The predefined range may be 0°-120°, for example 0°-100°, in particular 0°-90°. This may allow adjustment of the viewing direction of the at least one sensor within a predefined range, thereby potentially ensuring that a predefined volume within the room in which the device 1102 is arranged can be captured by the at least one sensor.

The cylindrical surface portion 1142 may comprise at least one first recess 1152, 1154. At least one of the retaining members 1148, 1150 may be configured to snap into the at least one first recess 1152, 1154 upon the housing 1104 being rotated by a maximum rotation angle of the predefined range of rotation angles. According to FIG. 13, two first recesses 1152, 1154 are provided, on associated with each of the two retaining members 1148, 1150. The at least one first recess 1152, 1154 and the at least one retaining member 1148, 1150 may be configured to avoid a rotation of the housing 1104 beyond the predefined rotation angle.

The holding portion 1124, in particular the cylindrical surface portion 1142, may comprise at least one locking member 1157, 1158. The housing 1104 may comprise at least one second recess 1160, 1162 matching the at least one locking member 1157, 1158. In the shown example, the recess 1160 matches the locking member 1157 and the recess 1162 matches the locking member 1158. The locking member(s) 1157, 1158 and the second recess(es) 1160, 1162 may be configured to couple to one another such that a relative translational movement between the housing 1104 and the holding portion 1124 the first rotation axis 1128 is blocked. Each of the at least one locking member 1157, 1158 may be configured as a guide rail guiding the at least one second recess 1160, 1162 such that the housing 1104 can be rotated around the rotation axis 1128.

The device 1102 may further comprise at least one orientation sensor 1115 configured to acquire orientation data representing an orientation of the housing 1104, wherein, as an option, the orientation is relative to at least one of the retainer 1120 and a direction of the earth's gravity. The sensor 1115 may correspond to the orientation sensor described above (e.g., the orientation sensor 49).

The coupling portion 1122 may be configured to be coupled to the mounting 1126 in only one or only two predefined relative orientations between the mounting 1126 and the retainer 1120. This may ensure that the retainer 1120 is arranged on a ceiling or wall, to which the mounting 1126 is fixed, in a predefined pose. This may be particularly advantageous if the device 1102 is removed after a first installation on the mounting 1126 and needs to be coupled thereto at a later point in time.

Figure 14:
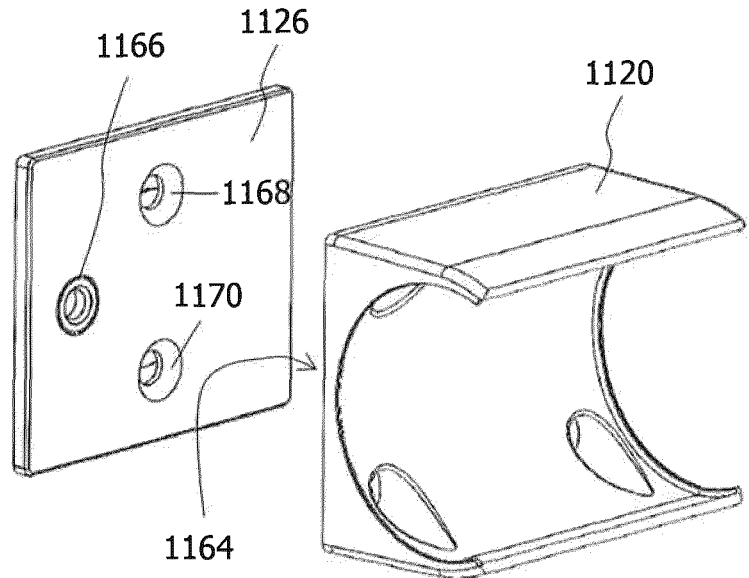
FIG. 14 shows a retainer of a monitoring device separated from a mounting.

FIG. 14 shows an illustration of the retainer 1120 removed from the mounting 1126. The coupling portion 1122 may comprise at least one first coupling element 1164 (hidden in FIG. 14) matching at least one second coupling element 1166 of the mounting 1126. The first coupling element 1164 and the second coupling element 1166 may form a magnetic coupling. At least one of the first coupling element 1164 and the second coupling element 1166 may comprise a magnet. At least one of the first coupling element 1164 and the second coupling element 1166 may comprise a ferromagnetic element. The mounting 1126 is configured to be attached to a wall or a ceiling of a room. The mounting 1126 may comprise one or more fixation holes 1168, 1170 for fixing the mounting 1126 to a wall or a ceiling, for example using screws.

Figure 15:
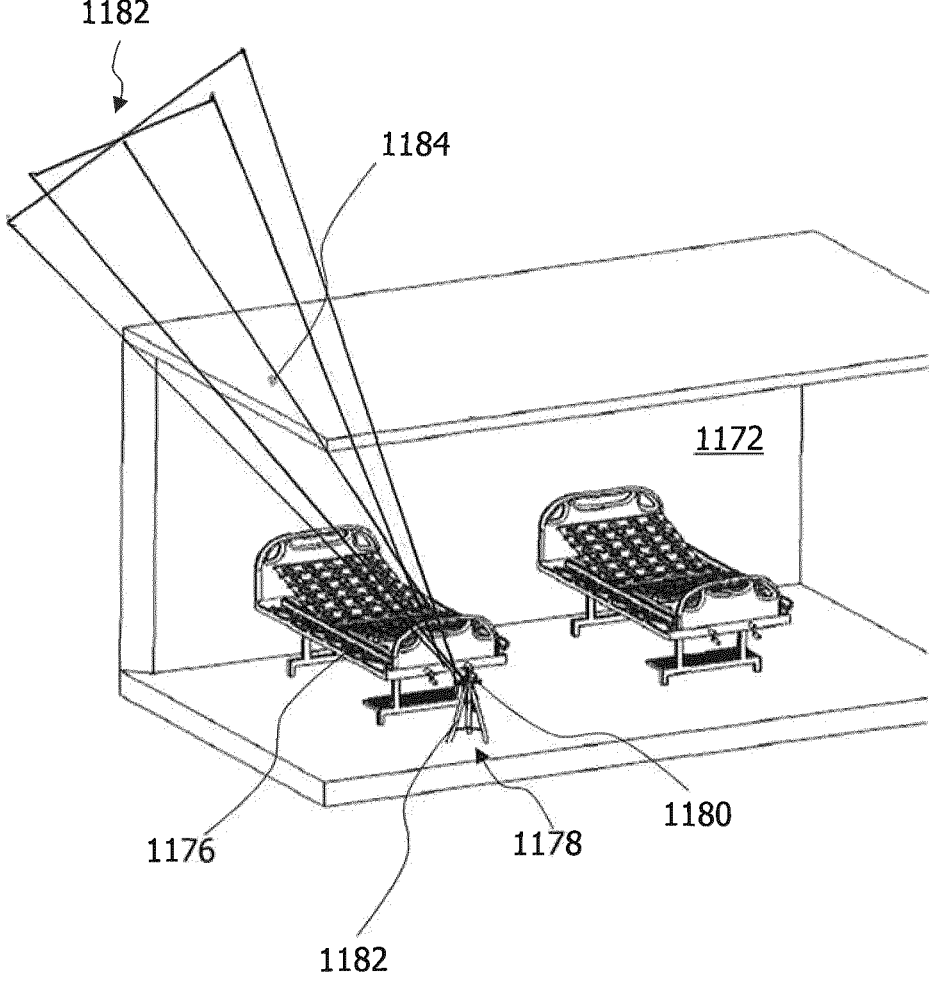
FIG. 15 shows an alignment apparatus arranged in a patient room.

FIG. 15 shows an illustration of a room 1172 in which a patient bed 1174 is arranged. The room 1172 may be a room of a hospital. The bed 1176 may correspond to the bed 14. An alignment apparatus 1178 is arranged in the room 1172 next to the bed 1176. In the shown example, the apparatus 1178 is positioned at a foot end of the patient bed 1176. The apparatus 1178 may be aligned with the patient bed 1176 in a predefined relative orientation. The alignment apparatus 1178 is configured to project a light pattern onto a ceiling or wall informing an installer where to attach the retainer 1120 or the mounting 1126 to the wall or the ceiling. To this end, the apparatus 1178 may comprise a light projecting unit 1180. The light projecting unit 1180 may be arranged on a stand 1180.

In the illustrated example, a cross-like projection pattern 1182 is emitted by the alignment apparatus 1178. The pattern is for example projected into a predefined direction relative to the patient bed 1176. The pattern may be projected onto the ceiling of the room 1172. The pattern may designate an area or point 1184 on the ceiling where at least one of the mounting 1126 or the retainer 1120 are to be attached or arranged. An installer may then fix the mounting 1126 in the area or at the point 1184 on the ceiling designated by the light pattern. This may ensure a proper field of view of the sensor(s) of the device 1102 (e.g., covering at least a portion, for example a predefined portion, of the patient bed 1176).

Figure 16:
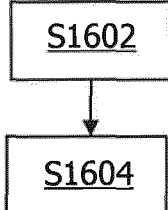
FIG. 16 shows a method of using an alignment apparatus.

The present disclosure therefore provides for the method illustrated in FIG. 16. The method in accordance with FIG. 16 is a method of arranging a mounting (e.g., the mounting 1126) for or a retainer (e.g., the retainer 1120) of a clinical monitoring device (e.g., the device 1102) in a room (e.g., the room 1172). The method comprises a step 1602 of using the alignment apparatus 1178 to project a light pattern onto the wall or the ceiling of the room. The method further comprises a step 1604 of attaching the retainer or the mounting to the wall or the ceiling of the room at a location (e.g., the area or point 1184) indicated or designated by the projected light pattern.

Figure 17:
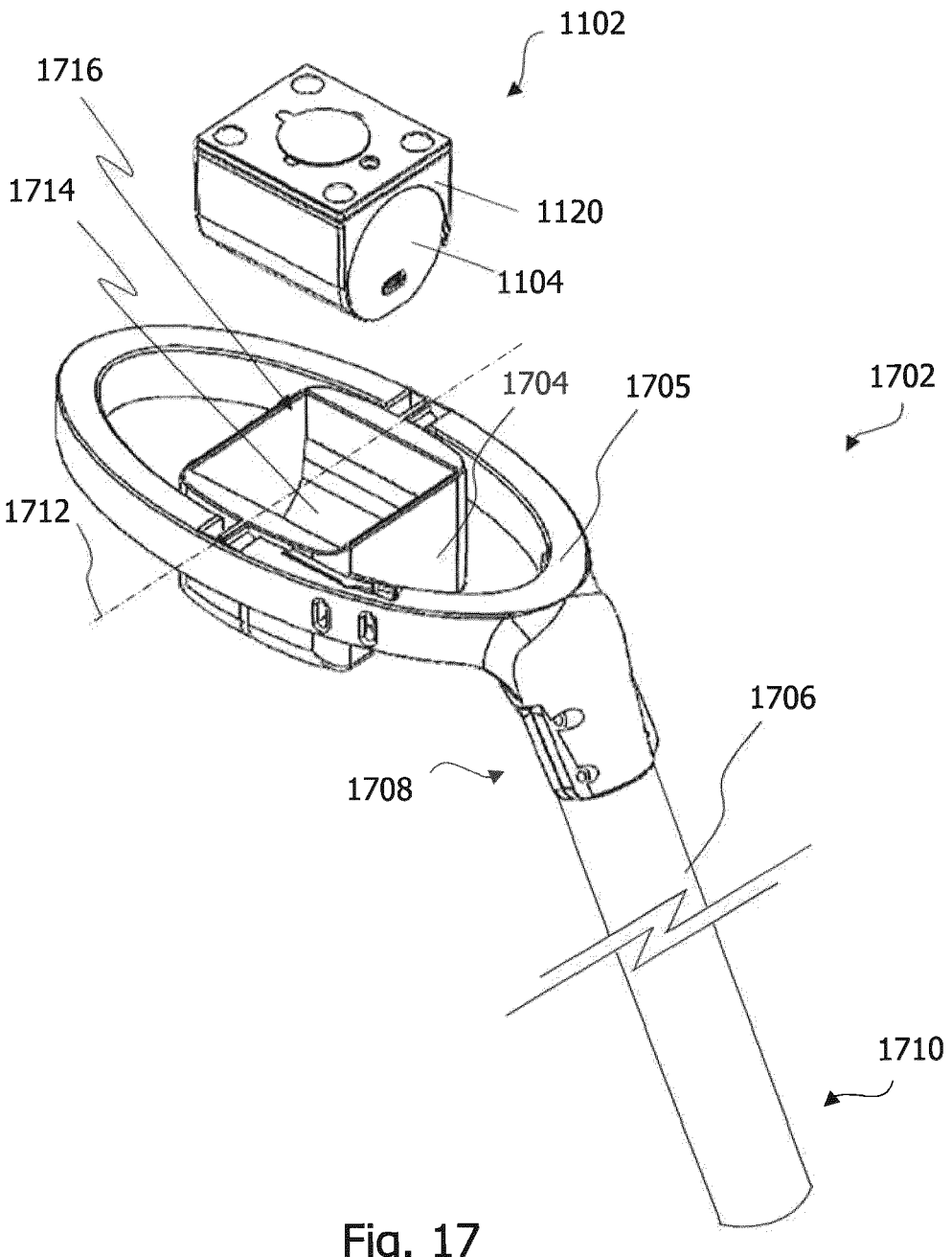
FIG. 17 shows a placement tool and a monitoring device.
Figure 18:
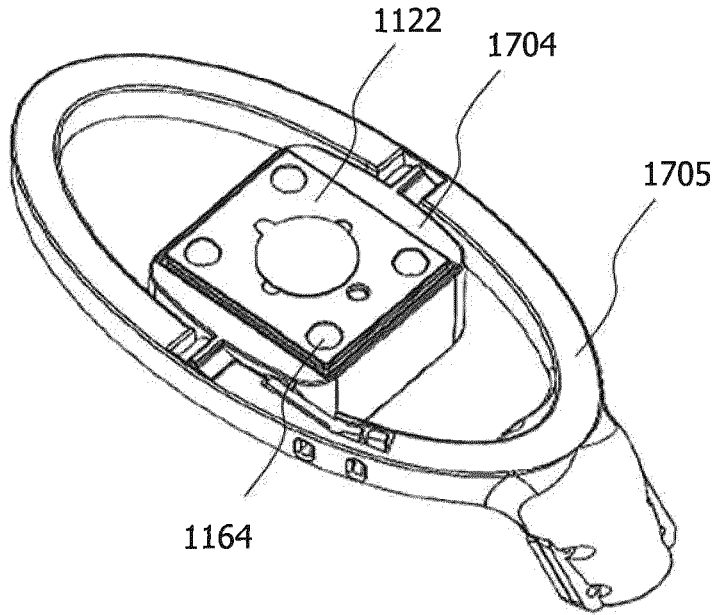
FIG. 18 shows a top view of a placement tool holding a monitoring device.
Figure 19:
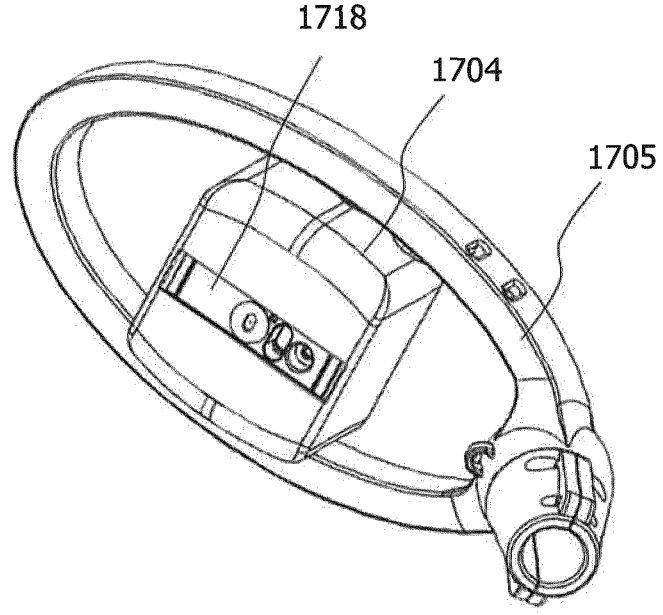
FIG. 19 shows a bottom view of a placement tool holding a monitoring device.

The present disclosure further provides for a mounting tool 1702 for use with the clinical monitoring device 1102. The mounting tool 1702 comprises a holder 1704 configured to removably hold the clinical monitoring device 1702. FIG. 17 shows the mounting tool 1720 with the device 1102 removed, and FIGS. 18 and 19 show toe different views of the device 1102 being held by the holder 1704 of the mounting tool 1702.

The mounting tool 1702 comprises a connector 1705 connected (e.g., coupled or movably fixed) to the holder 1704. The tool 1702 comprises an elongate rod 1706 having a first end 1708 and an opposite second end 1710. The first end 1708 is fixed (e.g., relative) to the connector 1705. The second end 1710 is configured to be grabbed by a user to move the holder 1704 with the device 1102 and couple the device 1102 in the holder 1704 to the mounting 1126. This may allow the user to couple the device 1102 onto the mounting 1126 even if the mounting 1126 is out of reach for the user's hands. In case the mounting 1126 is fixed to the ceiling, using the mounting tool 1720 may prevent the user from having to use a ladder to couple the device 1102 onto the mounting 1126. This may be particularly advantageous in clinical scenarios, where ladders might not be allowed to be used or only allowed to be used by certified personnel. A rotation of the holder 1704 relative to the connector 1705 may allow coupling the coupling portion 1122 to the mounting 1126 without having to precisely align the two components.

The holder 1704 may be configured to be rotatable relative to the rod 1706 around a second rotation axis 1712. The holder 1704 may be configured to be rotatable relative to the connector 1705 around the second rotation axis. The connector 1705 may be fixed (e.g., relative) to the elongate rod 1706. The second rotation axis 1712 may be perpendicular to at least one of a longitudinal axis of the rod 1706, the first rotation axis 1128 and the cylinder axis 1142. The holder 1704 may be configured to hold the device 1102 such that the coupling portion 1122 is oriented towards the sky, irrespective of a rotation of the rod 1706 relative to the holder 1704 (e.g., within a predefined range of rotation) around the second rotation axis 1712. Such a configuration may allow an easy coupling of the coupling portion 1122 to the mounting 1126, in particular if the mounting 1126 is fixed to a ceiling of a room.

The holder 1704 may have an inner surface portion 1714 matching an outer surface portion (e.g., a portion of the outer surface) of at least one of the housing 1104 and the retainer 1120. This may ensure a safe and reliable holding of the device 1102 by the holder 1704.

The holder 1704 may be configured such that the second rotation axis 1714 is arranged at an open end 1716 of the holder 1704, wherein the device 1102 is to be inserted into the open end 1716 for being held by the holder 1704. When the open end 1716 is directed toward the sky, a center of gravity of the device 1102 may be lower than the second rotation axis 1714. This may ensure that the open end 1716 is automatically oriented toward the sky by the gravitational force acting upon the device 1102 held within the holder 1740.

The holder 1704 may comprise an opening or recess 1718 configured to be arranged next to the device 1102 when the device 1102 is held by the holder 1704. The opening or recess 1718 may be configured such that one or more of (i) the at least one sensor 1108, 1110, 1112, 1114, (ii) the at least one opening 1130, 1132, 134, 1136 or (iii) the first side 1106 are arranged adjacent to or facing the opening or recess 1718 when the device 1102 is held by the holder 1704. This may avoid a damage or contamination (e.g., by dirt within the holder 1704) of the respective parts of the device 102.

Figure 20:
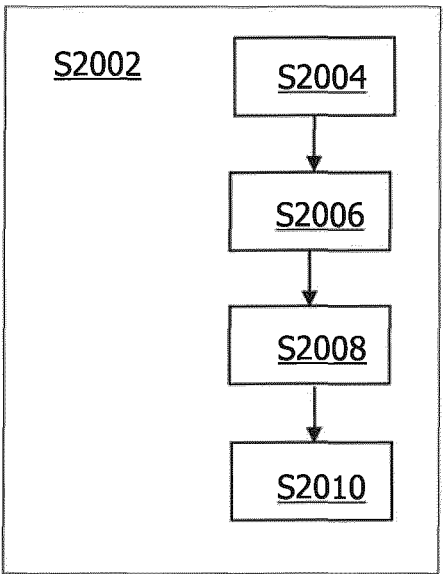
FIG. 20 shows a method of using a placement tool to arrange a monitoring device in a room.

The present disclosure also provides for a method as illustrated in FIG. 20. The method in accordance with FIG. 20 is a method arranging a clinical monitoring device (e.g., the device 1102) in a room (e.g., the room 1172). The method comprises a step S2002 of using the mounting tool 1702 to arrange the device 1102 in a room.

The method may comprise a step 2004 of providing the mounting 1126, wherein the mounting 1126 is attached to a wall or a ceiling of the room. The method may comprise a step 2006 of placing the device 1102 in the holder 1704 of the mounting tool 1702. The method may comprise a step S2010 of (e.g., grabbing and) moving the elongate rod 1706 such that the coupling portion couples to the mounting.

The method may comprise a step S2008 of providing a preferred rotation angle between the housing 1104 and the holding portion 1124 with respect to the first rotation axis 1128, before moving the elongate rod 1706 such that the coupling portion 1122 couples to the mounting 1126.

One or more of the steps S2004-S2010 may be part of step S2002.

In the following, further advantageous examples are briefly described. The reference signs indicate to which of the structural or functional features described above the respective term of the examples may correspond. It is in particular possible to use the device 20 or the device 1102 as described above as the device mentioned in the examples. The reference signs of the following examples are placed in parentheses, as the respective terms of the examples do not necessarily need to correspond to the structural or functional features described above. The devices, systems and methods of the following examples may not comprise all features described above with reference to the figures.

Example 1. A clinical monitoring device (20), in particular a patient zone monitoring device, comprising:
  a first sensing unit (34) comprising at least one first sensor (36) configured to acquire (e.g., the) spatial data (e.g., representing 3-dimensional information with respect to a first field of view (38) of the first sensing unit (34)); and
  a processing unit (30) comprising at least one processor, the processing unit (30) being configured to receive the spatial data from the sensing unit (34) and process the spatial data (34) in order to generate scene data.

According to example 1, the scene data may represent information with respect to a scene in the first field of view (38) of the sensing unit (34), wherein the scene data represents information that relates to at least one of presence of at least one patient bed (14), occupation of at least one patient bed (14), presence of at least one clinical device (18), presence of at least one patient (16), and presence of at least one person, in particular clinical personnel (44), in the first field of view (38) of the sensing unit (38). The device (20) according to example 1 may comprise a transmission/reception unit (32) configured to receive the scene data from the processing unit (30) and transmit the scene data over a communication network (100).

Example 2. The monitoring device (20) according to example 1,
  wherein the scene data represents information regarding at least one of a temporal and a spatial relationship between at least two different objects present in the first field of view (38).

Example 3. The monitoring device (20) according to example 1 or example 2,
  wherein the processing unit (30) is configured to generate the scene data based upon an analysis of spatial data acquired at different times.

Example 4. The monitoring device (20) according to at least one of the preceding examples,
  wherein the processing unit (30) is configured to generate, on the basis of the spatial data, the scene data based upon estimating the positions of at least two different objects in the first field of view (38), and based upon at least one of estimated volumes, estimated footprints and estimated surfaces of the at least two different objects.

Example 5. The monitoring device (20) according to at least one of the preceding examples,
  wherein the transmission/reception unit (32) is configured to determine at least one of an ID and a distance of at least one of a clinical personnel beacon (56), a patient beacon (58), a patient bed beacon (59) and a clinical device beacon (62), and
  wherein the processing unit is configured to receive at least one of said ID and said distance from the transmission/reception unit and generate the scene data in addition based upon at least one of said ID and said distance.

Example 6. The monitoring device (20) according to example 5,
  wherein the transmission/reception (32) unit is configured to operate using a low-energy protocol.

Example 7. The monitoring device (20) according to at least one of the preceding examples,
  wherein the processing unit (30) is configured to generate the scene data additionally based upon at least one of an identity and a distance of at least one of a clinical personnel (44), a patient (16), a patient bed (14) and a clinical device (18) determined from the spatial data.

Example 8. The monitoring device (20) according to at least one of the preceding examples,
  wherein the processing unit (30) is configured to determine, on the basis of the spatial data, at least one of an estimated height level of a floor and an estimated height level of a bed surface of a patient bed (14).

Example 9. The monitoring device (20) according to at least one of the preceding examples,
  wherein the device (20) comprises:
  a passive sensor (43) having a third field of view (45); and
  an active sensor (36) having the first field of view (38);
  wherein the third field of view (45) and the first field of view (38) overlap, and
wherein the processing unit (30) is configured for generating a wake-up signal for the active sensor (36) causing a wake-up operation of the active sensor (36).

Example 10. The monitoring device (20) according to example 9,
  wherein the processing unit (30) is configured to generate the wake-up signal depending upon at least one of detection of an object in the third field of view (45) by the passive sensor (43) and reception of a sensing demand signal from the communication network (100).

Example 11. The monitoring device (20) according to example 9 or example 10,
  wherein the processing unit (30) is configured to generate a sleep-mode signal for the active sensor (36) causing the active sensor (36) to transition into a sleep mode,
  wherein the processing unit (30) is configured to generate the sleep-mode signal depending upon at least one of a time period of activation of the active sensor (36), a time-period of not detecting an object by the passive sensor (43), an availability of operational power, and a reception of a sleep demand signal from the communication network (100).

Example 12. The monitoring device (20) according to at least one of examples 9 to 11,
  wherein the passive sensor is an infrared sensor.

Example 13. The monitoring device (20) according to at least one of examples 9 to 12,
  wherein the active sensor is a time-of-flight sensor.

Example 14. The monitoring device (20) according to at least one of examples 9 to 13,
  wherein the third field of view is larger than the first field of view.

Example 15. The monitoring device (20) according to at least one of the preceding examples, further comprising an energy storage unit (26) configured to provide operational power allowing the monitoring device (20) to be fully operational independently of an electricity grid.

Example 16. The monitoring device (20) according to at least one of the preceding examples, further comprising an energy harvesting unit (28) configured to harvest energy from an indoor environment.

Example 17. The monitoring device (20) according to at least one of the preceding examples, wherein the processing unit (30) is configured to generate the scene data such that it represents information regarding at least one of the following: presence of an empty patient bed (14); presence of an occupied patient bed (14); presence of an empty patient bed (14) of a certain type; presence of an occupied patient bed (14) of a certain type; presence of a clinical device (18); presence of a clinical device (18) of a certain type; presence of at least one person; presence and identity of at least one person; presence of clinical personnel (44); presence and identity of clinical personnel; interaction between clinical personnel (44) and a patient (16); interaction between clinical personnel (44) and a patient zone; presence of clinical personnel (44) before an interaction with a patient (16); presence of clinical personnel (44) after interaction with a patient (16); presence of clinical personnel (44) after interaction with a patient zone; absence of clinical personnel (44) after interaction with the patient (16); absence of clinical personnel (44) after interaction with the patient zone; presence of clinical personnel (44) before an aseptic activity; presence of clinical personnel (44) after an aseptic activity; presence of a patient in a certain acute condition; amount of movement of a patient during a certain time period; and presence of a patient who has fallen out of a bed.

Example 18. The monitoring device (20) according to at least one of the preceding examples, further comprising a housing (22) with a mounting unit (24), wherein the housing (22) houses at least the sensing unit (34), the processing unit (30) and the transmission/reception unit (32), and wherein the mounting unit (24) is configured to be affixed to at least one of a ceiling (14) and a wall (12).

Example 19. A clinical monitoring system (60), comprising:

at least one monitoring device (20) according to at least one of the preceding examples; and a monitoring unit (66) comprising at least one processor, the monitoring unit (66) being configured to receive the scene data from the monitoring device (20) and process the scene data.

Example 20. The monitoring system (60) according to example 19, further comprising a server (78) comprising the monitoring unit (66).

Example 21. The monitoring system (60) according to example 19, further comprising a mobile terminal (80) comprising the monitoring unit (66).

Example 22. The monitoring system (60) according to at least one of examples 19 to 21, wherein the monitoring device (20) is arranged in an area of concern (70-76), the clinical monitoring system further comprising:

at least one portable device (64);

at least one hygiene dispenser (59) arranged in the area of concern (70-76); and at least one treatment detection unit (60) configured to detect a disinfection treatment performed with the hygiene dispenser (59), identify the portable device (64), and generate treatment data representing information regarding the detected treatment and the identified portable device (64); and wherein the monitoring unit (60) is further configured to receive the treatment data from the treatment detection unit (63) and determine a hygiene status based upon the treatment data and the scene data, and assign the hygiene status to the portable device (64).

Example 23. The monitoring system (60) according to example 22, wherein the portable device (64) is configured to receive the hygiene status from the monitoring unit (66) and to generate at least one perceptible output indicative of the hygiene status.

Example 24. The monitoring system (60) according to example 22 or example 23, further comprising at least one output device (68) arranged in the area of concern (74-76), the output device (68) being configured to receive the hygiene status from the monitoring unit (66) and to generate at least one perceptible output indicative of the hygiene status.

Example 25. The monitoring system (60) according to example 23 or example 24, wherein the perceptible output comprises at least one of an audio signal, a haptic signal, a visual signal, a vibration signal, an image, an animation and a light color.

Example 26. The monitoring system (60) according to at least one of examples 22 to 25, wherein the monitoring unit (66) is configured to modify the scene data received from the monitoring device (20) such that it represents information regarding at least one of the following: presence of an empty patient bed; presence of an occupied patient bed; presence of an empty patient bed of a certain type; presence of an occupied patient bed of a certain type; presence of a clinical device; presence of a clinical device of a certain type; presence of at least one person; presence and identity of at least one person; presence of clinical personnel; presence and identity of clinical personnel; interaction between clinical personnel and a patient; interaction between clinical personnel and a patient zone; presence of clinical personnel before an interaction with a patient; presence of clinical personnel after interaction with a patient; presence of clinical personnel after interaction with a patient zone; absence of clinical personnel after interaction with the patient; absence of clinical personnel after interaction with the patient zone; presence of clinical personnel before an aseptic activity; presence of clinical personnel after an aseptic activity; presence of a patient in a certain acute condition; amount of movement of a patient during a certain time period; and presence of a patient who has fallen out of a bed.

Example 27. The monitoring system (60) according to at least one of examples 22 to 26, wherein the monitoring unit (66) is further configured to: determine, on the basis of the scene data, that clinical personnel (44) is in at least one of the following situations: before interaction with a patient (16), before an aseptic activity, after contact to infectious material, after interaction with a patient (16), and after interaction with a patient zone; and determine, on the basis of the treatment data, whether or not clinical personnel (44) has sanitized hands before or in said situation.

Example 28. The monitoring system (60) according to at least one of examples 19 to 27, further comprising:

a plurality of monitoring devices (20), each according to at least one of examples 1 to 18, the monitoring devices (20) being arranged in different areas of concern (70, 72, 74, 76);

wherein the monitoring unit (66) is configured to receive scene data from each of the plurality of monitoring devices (20), and generate, on the basis of the received scene data, bed occupation data representing information regarding presence and occupation state of different patient beds (14) present in the different areas of concern (70, 72, 74, 76); and an output unit (81) configured to receive the bed occupation data from the monitoring unit (66) and output the bed occupation data to a user.

Example 29. The monitoring system (60) according to example 28, wherein the monitoring unit (66) is configured to extract from the scene data a bed type for each of the patient beds (14) and include bed type information in the bed occupation data.

Example 30. The monitoring system (60) according to example 28 or example 29, wherein the output unit (83) is part of a user interface configured to receive user input, and wherein the monitoring unit (66) is configured to generate the bed occupation data based upon the user input such that the output of the bed occupation data is interactive.

Example 31. The monitoring system (60) according to at least one of examples 19 to 30, wherein the monitoring unit (66) is configured to generate, on the basis of the scene data, patient monitoring data, the monitoring system (60) further comprising an output unit (83) configured to receive the patient monitoring data from the monitoring unit (66) and output the patient monitoring data to a user.

Example 32. The monitoring system (60) according to example 31, wherein at least one of the processing unit (30) of the monitoring device (20) and the monitoring unit (66) is configured to evaluate a temporal evolution of height information of a region associated with a patient with respect to a region associated with a surface of a patient bed, and to determine an amount of patient movement over time based upon said temporal evolution.

Example 33. The monitoring system (60) according to example 31 or example 32, wherein at least one of the processing unit (30) of the monitoring device (20) and the monitoring unit (66) is configured to determine a breathing rate by tracking movement of the patient and in particular of an area associated with a chest of a patient over time; and wherein the monitoring unit (66) is configured to generate the patient monitoring data on the basis of the determined breathing rate.

Example 34. The monitoring system (60) according to at least one of examples 31 to 33, wherein the patient monitoring data represents information regarding a risk for pressure sores.

Example 35. A clinical method using a monitoring system (60) according to at least one of examples 19 to 34, comprising:

generating, with the monitoring device (20), scene data;

receiving, with the monitoring unit (66), the scene data;

processing, with the monitoring unit (66), the scene data.

Example 36. A clinical method for monitoring hygiene compliance using a monitoring system (60) according to at least one of examples 22 to 27, comprising:

providing clinical personnel (44) with the portable device (64);

detecting, with the treatment detection unit (63), a disinfection treatment performed by the clinical personnel (44) due to identification of the portable device (64);

generating, with the treatment detection unit (63), treatment data representing information regarding the detected treatment and the identified portable device (64);

generating, with the monitoring device (20), scene data relating to the area of concern (70, 72, 74, 76);

receiving, with the monitoring unit (66), the treatment data and the scene data;

determining, with the monitoring unit (66), a hygiene status based upon the treatment data and the scene data; and assigning, with the monitoring unit (66), the hygiene status to the portable device (64).

Example 37. The clinical method according to example 36, further comprising:

determining, on the basis of the scene data, that clinical personnel (44) is in at least one of the following situations: before interaction with a patient (16), before an aseptic activity, after contact to infectious material, after interaction with a patient (16), and after interaction with a patient zone; and determining, on the basis of the treatment data, whether or not clinical personnel 44 has sanitized hands before or in said situation.

Example 38. A clinical method for monitoring availability and occupation of patient beds in a medical facility using a monitoring system (60) according to at least one of examples 28 to 30, comprising:

generating, with the plurality of monitoring devices (20), respective scene data relating to the different areas of concern (70, 72, 74, 76);

receiving, with the monitoring unit (66), the scene data from each of the plurality of monitoring devices (20);

generating, with the monitoring unit (66), bed occupation data representing information regarding presence and occupation state of different patient beds (14) present in the different areas of concern (70, 72, 74, 76);

receiving, with the output unit (83), the bed occupation data from the monitoring unit (66); and outputting, with the output unit (83), the bed occupation data to a user.

Example 39. A clinical method for patient monitoring using a monitoring system (60) according to at least one of examples 31 to 34, comprising:

generating, with the monitoring device (20), scene data;

receiving, with the monitoring unit (66), the scene data;

generating, with the monitoring unit (66), patient monitoring data on the basis of the scene data;

receiving, with the output unit (83), the patient monitoring data; and outputting, with the output unit (83), the patient monitoring data.

Example 40. A clinical method, in particular a patient zone monitoring method, comprising:

acquiring spatial data representing 3-dimensional information with respect to a first field of view (38) of the sensing unit (34);

processing the spatial data in order to generate scene data representing information with respect to the scene in the first field of view (38) of the sensing unit (34), wherein the scene data represents information that relates to at least one of presence of at least one patient bed (14), occupation of at least one patient bed (14), presence of at least one clinical device (18), presence of at least one patient (16), and presence of at least one person, in particular clinical personnel (44), in the first field of view (38) of the sensing unit (34); and transmitting the scene data over a communication network (100).

Example 41. A clinical method, in particular a patient zone monitoring method, comprising:

receiving scene data over a communication network (100), the scene data representing information that relates to at least one of presence of a patient bed (14), occupation of a patient bed (14), presence of at least one clinical device (18), presence of a patient (16) and presence of clinical personnel (44) in the field of view of the sensing unit (34).

The invention claimed is:

1. A clinical monitoring device, in particular a patient zone monitoring device, comprising:

a first sensing unit comprising at least one first sensor configured to acquire spatial data representing spatially resolved depth information with respect to a first field of view of the first sensing unit;

a second sensing unit comprising at least one second sensor configured to acquire thermal data representing spatially resolved temperature information with respect to a second field of view of the second sensing unit; and a processing unit comprising at least one processor, the processing unit being configured to receive the spatial data from the first sensing unit and the thermal data from the second sensing unit and process at least the spatial data and the thermal data to generate scene data representing information with respect to a scene in a volume comprised in at least one of the first field of view and the second field of view.

2. The device of claim 1, wherein:

the scene data includes information on at least one of presence, class and properties of one or more objects within the volume.

3. The monitoring device of claim 1, wherein:

the first field of view at least partially overlaps the second field of view.

4. The monitoring device of claim 3, wherein:

the first field of view overlaps the second field of view at least or only in the volume.

5. The monitoring device of claim 4, wherein the processing unit is configured to:

determine the volume where the first field of view overlaps the second field of view;

select at least one of:

(i) from the spatial data, a portion of the spatial data representing spatially resolved depth information with respect to the volume, and (ii) from the thermal data, a portion of the thermal data representing spatially resolved temperature information with respect to the volume; and determine the scene data based on the at least one selected portion.

6. The monitoring device of claim 5, further comprising:

at least one of a mask and a lens arranged such that it defines at least one of the first field of view and the second field of view, wherein the processing unit is configured to determine the volume based on information related to the at least one of the mask and the lens.

7. The monitoring device of claim 4, wherein:

the processing unit is configured to generate the scene data by (i) analyzing the spatial data to detect an object present in the volume, and by (ii) comparing, based on the thermal data, a temperature of one or more surface areas of the detected object with at least one predefined thermal property associated with at least one object class to classify the detected object.

8. The monitoring device of claim 1, wherein:

the processing unit is configured to generate the scene data based upon an analysis of at least one of spatial data acquired at different times and thermal data acquired at different times.

9. The monitoring device of claim 8, wherein:

the processing unit is configured to generate the scene data by (i) analyzing the spatial data to detect an object present in the volume, and by (ii) comparing, based on the thermal data acquired at different times, a temporal temperature behavior of one or more surface areas of the detected object with at least one predefined thermal property associated with at least one object class to classify the detected object.

10. The monitoring device of claim 1, wherein:

the scene data represents information regarding at least one of a temporal and a spatial relationship between at least two different objects present in the volume.

11. The monitoring device according to claim 10, wherein:

one of the at least two different objects is an occupied patient bed and another one of the at least two different objects is a person, wherein the scene data represents information that relates to the person bending over the occupied patient bed.

12. The monitoring device of claim 1, wherein:

the scene data represents information that relates to at least one of presence of at least one patient bed, presence of at least one occupied patient bed, presence of at least one clinical device, presence of at least one patient, and presence of at least one person, in particular clinical personnel, in the volume.

13. The monitoring device of claim 1, further comprising an orientation sensor configured to acquire orientation data representing an orientation of the monitoring device, wherein the processing unit is configured to:

obtain height information indicating a distance, in particular a minimal distance, between the monitoring device and a floor; and determine, on the basis of the orientation data and the height information, pose data indicative of a position and orientation of the monitoring device relative to the floor.

14. The monitoring device of claim 13, wherein:

the processing unit is configured to:

determine, on the basis of the spatial data and the pose data, an estimated height level of one or more surfaces of an object present within the volume, the estimated height level being determined relative to the floor; and generate the scene data based on the estimated height level.

15. The monitoring device according to claim 1, further comprising:

a third sensing unit comprising at least one passive sensor configured to generate a sensing signal responsive to an object entering or exiting a third field of view of the third sensing unit, wherein the processing unit is configured to receive the sensing signal from the third sensing unit and generate the scene data further based on the sensing signal, wherein the scene data represents information with respect to a scene in both the volume and the third field of view.

16. The monitoring device of claim 15, wherein:

the processing unit is configured for generating a wake-up signal for at least one sensor selected from the first sensor and the second sensor, the wake-up signal causing a wake-up operation of the at least one sensor, and the processing unit is configured to generate the wake-up signal responsive to the passive sensor generating the sensing signal.

17. The monitoring device according to claim 15, further comprising:

a fourth sensing unit comprising at least one luminosity sensor configured to acquire luminosity data representing an average luminosity with respect to a fourth field of view of the fourth sensing unit, wherein the processing unit is configured for generating a primary wake-up signal for the passive sensor, the primary wake-up signal causing a wake-up operation of the passive sensor, wherein processing unit is configured to generate the primary wake-up signal responsive to determining that a luminosity indicated by the luminosity information exceeded a predefined threshold for a predefined time.

18. The monitoring device of claim 16, wherein:

the wake-up operation of the respective sensor configures the respective sensor with a higher sensor sampling rate compared with a non-zero sensor sampling rate of the respective sensor before the wake-up operation.

19. A clinical monitoring system, comprising:

at least one clinical monitoring device, in particular a patient zone monitoring device, comprising:

a first sensing unit comprising at least one first sensor configured to acquire spatial data representing spatially resolved depth information with respect to a first field of view of the first sensing unit;

a second sensing unit comprising at least one second sensor configured to acquire thermal data representing spatially resolved temperature information with respect to a second field of view of the second sensing unit; and a processing unit comprising at least one processor, the processing unit being configured to receive the spatial data from the first sensing unit and the thermal data from the second sensing unit and process at least the spatial data and the thermal data to generate scene data representing information with respect to a scene in a volume comprised in at least one of the first field of view and the second field of view; and a monitoring unit comprising at least one processor, the monitoring unit being configured to receive the scene data from the monitoring device and process the scene data.

* * * * *